(12) United States Patent
Mumaw et al.

(10) Patent No.: US 9,782,164 B2
(45) Date of Patent: Oct. 10, 2017

(54) SUTURING INSTRUMENT WITH MULTI-MODE CARTRIDGES

(71) Applicant: Ethicon Endo-Surgery, LLC, Guaynabo, PR (US)

(72) Inventors: Daniel J. Mumaw, Liberty Township, OH (US); Christopher J. Hess, Cincinnati, OH (US); Frederick E. Shelton, IV, Hillsboro, OH (US); David T. Martin, Milford, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 120 days.

(21) Appl. No.: 14/740,834

(22) Filed: Jun. 16, 2015

(65) Prior Publication Data
US 2016/0367239 A1 Dec. 22, 2016

(51) Int. Cl.
*A61B 17/04* (2006.01)
*A61B 17/068* (2006.01)
(Continued)

(52) U.S. Cl.
CPC ...... *A61B 17/0469* (2013.01); *A61B 17/0467* (2013.01); *A61B 17/0482* (2013.01);
(Continued)

(58) Field of Classification Search
CPC .............. A61B 17/068; A61B 17/0682; A61B 17/0684; A61B 17/0686; A61B 17/122;
(Continued)

(56) References Cited

U.S. PATENT DOCUMENTS 4,027,608 A * 6/1977 Arbuckle ............... D05B 81/00
112/169
4,557,265 A * 12/1985 Andersson ......... A61B 17/0491
112/222
(Continued)

FOREIGN PATENT DOCUMENTS

EP 2 792 308 A2 10/2014

OTHER PUBLICATIONS

U.S. Appl. No. 14/297,993, filed Jun. 6, 2014
(Continued)

*Primary Examiner* — Ryan J Severson
(74) *Attorney, Agent, or Firm* — Frost Brown Todd LLC

(57) ABSTRACT

A surgical kit includes an instrument and two or more cartridges. The instrument includes a body, a shaft assembly, and a cartridge receiving assembly. The cartridge receiving assembly has a movable output feature, which is configured to move in response to activation of the actuation input feature. The cartridges may include a first suturing cartridge and a second suturing cartridge, with first and second suture needles, respectively. The second suture needle may extend along an arc that has a larger radius of curvature than an arc associated with the first suture needle. The cartridges may also include a drive assembly that is operable to drive the needle along an orbital path in response to movement of the actuation input feature. The cartridges may also include features that are operable to apply clips or staples. The cartridges may also include features that are operable to grasp or cut.

20 Claims, 32 Drawing Sheets

(51) Int. Cl.
*A61B 17/128* (2006.01)
*A61B 17/29* (2006.01)
*A61B 17/3201* (2006.01)
*A61B 17/32* (2006.01)
*A61B 17/28* (2006.01)
*A61B 17/285* (2006.01)
A61B 17/00 (2006.01)
A61B 17/06 (2006.01)

(52) U.S. Cl.
CPC .... *A61B 17/06066* (2013.01); *A61B 17/0682* (2013.01); *A61B 17/0684* (2013.01); *A61B 17/1285* (2013.01); *A61B 17/28* (2013.01); *A61B 17/285* (2013.01); *A61B 17/2816* (2013.01); *A61B 17/2841* (2013.01); *A61B 17/29* (2013.01); *A61B 17/320016* (2013.01); *A61B 2017/00464* (2013.01); *A61B 2017/0609* (2013.01)

(58) Field of Classification Search
CPC ... A61B 17/128; A61B 17/1285; A61B 17/29; A61B 17/320016; A61B 17/3201; A61B 2017/00464; A61B 2017/07214; A61B 2017/2926; A61B 2017/2931; A61B 2017/2938
See application file for complete search history.

(56) References Cited

U.S. PATENT DOCUMENTS

| | | | | |
|---|---|---|---|---|
| 4,899,746 A * | 2/1990 | Brunk | A61B 17/0491 | 112/169 |
| 5,709,693 A * | 1/1998 | Taylor | A61B 17/0491 | 606/139 |
| 5,766,186 A * | 6/1998 | Faraz | A61B 17/0469 | 606/145 |
| 5,911,727 A * | 6/1999 | Taylor | A61B 17/0491 | 606/139 |
| 6,443,962 B1 * | 9/2002 | Gaber | A61B 17/0491 | 112/80.04 |
| 7,004,951 B2 * | 2/2006 | Gibbens, III | A61B 17/0482 | 606/144 |
| 7,338,504 B2 * | 3/2008 | Gibbens | A61B 17/0482 | 606/144 |
| 7,628,796 B2 * | 12/2009 | Shelton, IV | A61B 1/00087 | 606/139 |
| 7,699,860 B2 | 4/2010 | Huitema et al. | | |
| 7,828,812 B2 * | 11/2010 | Stokes | A61B 1/00087 | 606/139 |
| 7,833,236 B2 * | 11/2010 | Stokes | A61B 1/00087 | 606/139 |
| 7,862,572 B2 * | 1/2011 | Meade | A61B 17/0482 | 606/145 |
| 7,887,554 B2 * | 2/2011 | Stokes | A61B 1/00087 | 606/139 |
| 7,976,553 B2 * | 7/2011 | Shelton, IV | A61B 1/00087 | 606/139 |
| 8,021,375 B2 | 9/2011 | Aldrich et al. | | |
| 8,123,764 B2 * | 2/2012 | Meade | A61B 17/0469 | 606/139 |
| 8,474,522 B2 * | 7/2013 | Lynde | E21B 21/002 | 166/99 |
| 8,500,756 B2 * | 8/2013 | Papa | A61B 1/00087 | 606/139 |
| 8,641,728 B2 * | 2/2014 | Stokes | A61B 1/00087 | 606/139 |
| 8,702,732 B2 | 4/2014 | Woodard et al. | | |
| 8,821,519 B2 * | 9/2014 | Meade | A61B 17/0469 | 606/139 |
| 8,906,043 B2 * | 12/2014 | Woodard, Jr. | A61B 17/0469 | 606/147 |
| 9,113,861 B2 * | 8/2015 | Martin | A61B 17/062 | |
| 9,125,645 B1 * | 9/2015 | Martin | A61B 17/0469 | |
| 9,168,037 B2 * | 10/2015 | Woodard, Jr. | A61B 17/0469 | |
| 9,220,496 B2 | 12/2015 | Martin et al. | | |
| 9,247,938 B2 * | 2/2016 | Martin | A61B 17/062 | |
| 9,277,916 B2 * | 3/2016 | Martin | A61B 17/0469 | |
| 9,357,998 B2 * | 6/2016 | Martin | A61B 17/0483 | |
| 9,375,212 B2 * | 6/2016 | Martin | A61B 17/0482 | |
| 9,427,226 B2 * | 8/2016 | Martin | A61B 17/0469 | |
| 9,451,946 B2 * | 9/2016 | Woodard, Jr. | A61B 17/0469 | |
| 2003/0083674 A1 * | 5/2003 | Gibbens, III | A61B 17/0482 | 606/144 |
| 2006/0069396 A1 * | 3/2006 | Meade | A61B 17/0482 | 606/144 |
| 2006/0111732 A1 * | 5/2006 | Gibbens | A61B 17/0482 | 606/145 |
| 2006/0281970 A1 * | 12/2006 | Stokes | A61B 1/00087 | 600/104 |
| 2006/0282090 A1 * | 12/2006 | Stokes | A61B 1/00087 | 606/144 |
| 2006/0282091 A1 * | 12/2006 | Shelton, IV | A61B 1/00087 | 606/144 |
| 2006/0282092 A1 * | 12/2006 | Stokes | A61B 1/00087 | 606/144 |
| 2006/0282093 A1 * | 12/2006 | Shelton, IV | A61B 1/00087 | 606/144 |
| 2006/0282094 A1 * | 12/2006 | Stokes | A61B 1/00087 | 606/144 |
| 2006/0282095 A1 * | 12/2006 | Stokes | A61B 1/00087 | 606/144 |
| 2006/0282096 A1 * | 12/2006 | Papa | A61B 1/00087 | 606/144 |
| 2006/0282098 A1 * | 12/2006 | Shelton, IV | A61B 1/00087 | 606/144 |
| 2006/0282099 A1 * | 12/2006 | Stokes | A61B 1/00087 | 606/148 |
| 2007/0239176 A1 * | 10/2007 | Stokes | A61B 17/00234 | 606/144 |
| 2007/0239177 A1 * | 10/2007 | Stokes | A61B 17/0469 | 606/144 |
| 2008/0255590 A1 * | 10/2008 | Meade | A61B 17/0482 | 606/144 |
| 2009/0108048 A1 * | 4/2009 | Zemlok | A61B 17/07207 | 227/175.1 |
| 2009/0209980 A1 * | 8/2009 | Harris | A61B 17/0491 | 606/144 |
| 2010/0152751 A1 * | 6/2010 | Meade | A61B 17/0469 | 606/144 |
| 2011/0278344 A1 * | 11/2011 | Zemlok | A61B 17/07207 | 227/176.1 |
| 2011/0313433 A1 | 12/2011 | Woodard et al. | | |
| 2012/0130404 A1 * | 5/2012 | Meade | A61B 17/0469 | 606/145 |
| 2012/0143223 A1 * | 6/2012 | Woodard, Jr. | A61B 17/0469 | 606/147 |
| 2012/0220989 A1 * | 8/2012 | Zemlok | A61B 17/07207 | 606/1 |
| 2012/0289975 A1 * | 11/2012 | Martin | A61B 17/062 | 606/147 |
| 2012/0290005 A1 | 11/2012 | Martin et al. | | |
| 2013/0245647 A1 * | 9/2013 | Martin | A61B 17/0469 | 606/147 |
| 2013/0245648 A1 * | 9/2013 | Martin | A61B 17/0469 | 606/147 |
| 2013/0282027 A1 * | 10/2013 | Woodard, Jr. | A61B 17/0469 | 606/144 |
| 2013/0282031 A1 * | 10/2013 | Woodard, Jr. | A61B 17/062 | 606/147 |
| 2014/0171970 A1 | 6/2014 | Martin et al. | | |
| 2015/0090764 A1 * | 4/2015 | Zemlok | A61B 17/07207 | 227/176.1 |
| 2015/0133967 A1 * | 5/2015 | Martin | A61B 17/0482 | 606/144 |
| 2015/0142020 A1 * | 5/2015 | Woodard, Jr. | A61B 17/0469 | 606/147 |
| 2015/0327857 A1 * | 11/2015 | Zemlok | A61B 17/07207 | 227/176.1 |

(56) References Cited

U.S. PATENT DOCUMENTS

| | | | | |
|---|---|---|---|---|
| 2015/0351748 A1* | 12/2015 | White | ................ | A61B 17/0482 |
| | | | | 606/145 |
| 2016/0120740 A1* | 5/2016 | Rawls-Meehan | .. | A61H 23/0263 |
| | | | | 601/49 |
| 2016/0249945 A1* | 9/2016 | Shelton, IV | ......... | A61B 17/068 |
| | | | | 606/171 |
| 2016/0367238 A1* | 12/2016 | Deck | .................. | A61B 17/0469 |
| 2016/0367243 A1* | 12/2016 | Martin | ............... | A61B 17/0469 |

OTHER PUBLICATIONS

U.S. Appl. No. 14/298,038, filed Jan. 30, 2015.
International Search Report and Written Opinion dated Nov. 14, 2016 for Application No. PCT/US2016/037350, 16 pgs.

\* cited by examiner

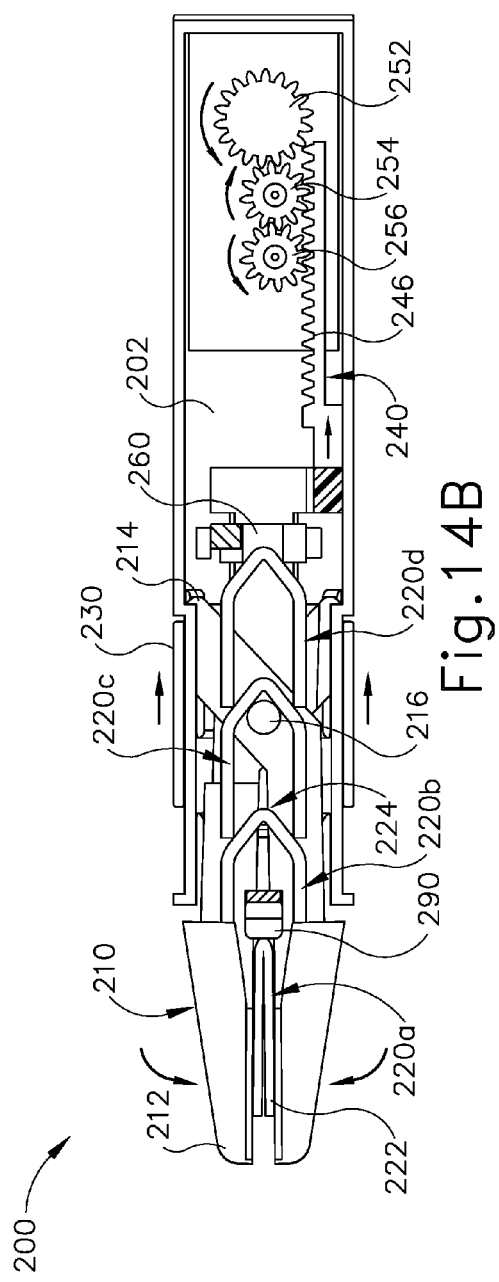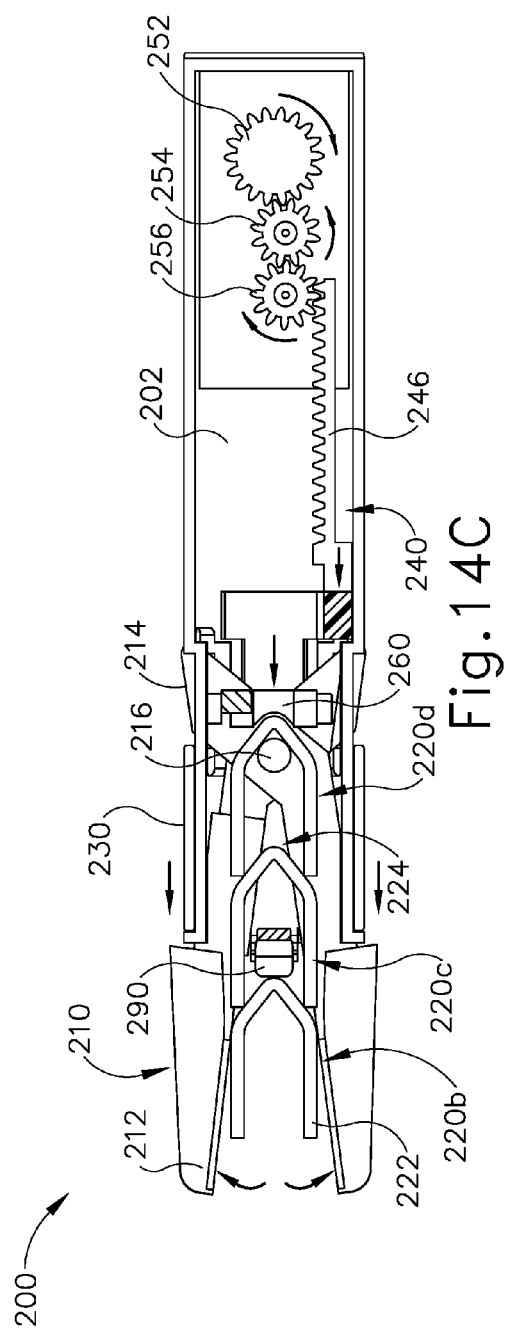

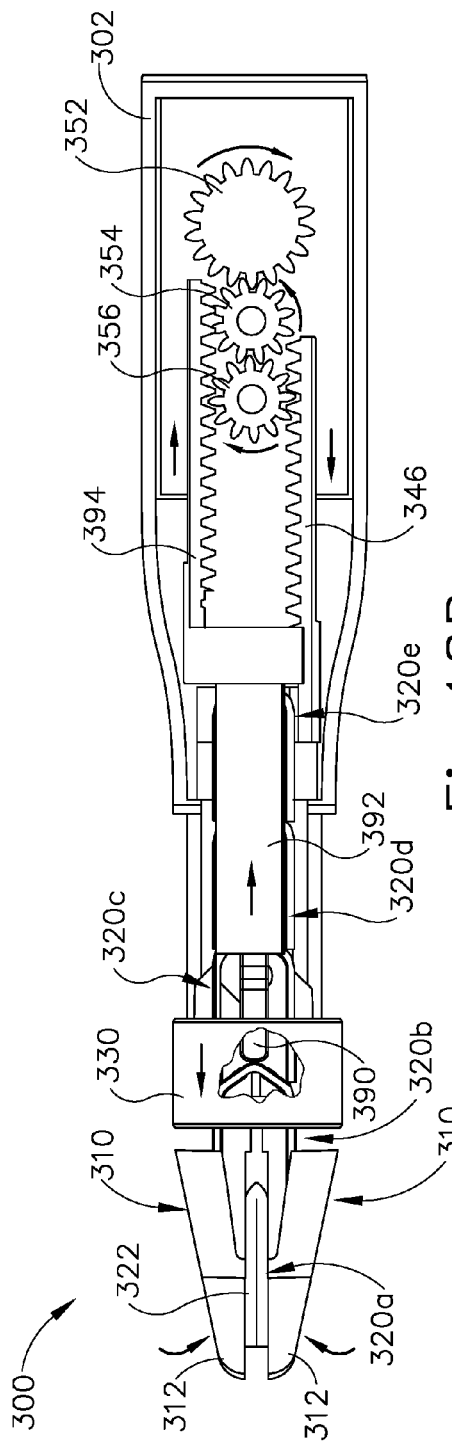
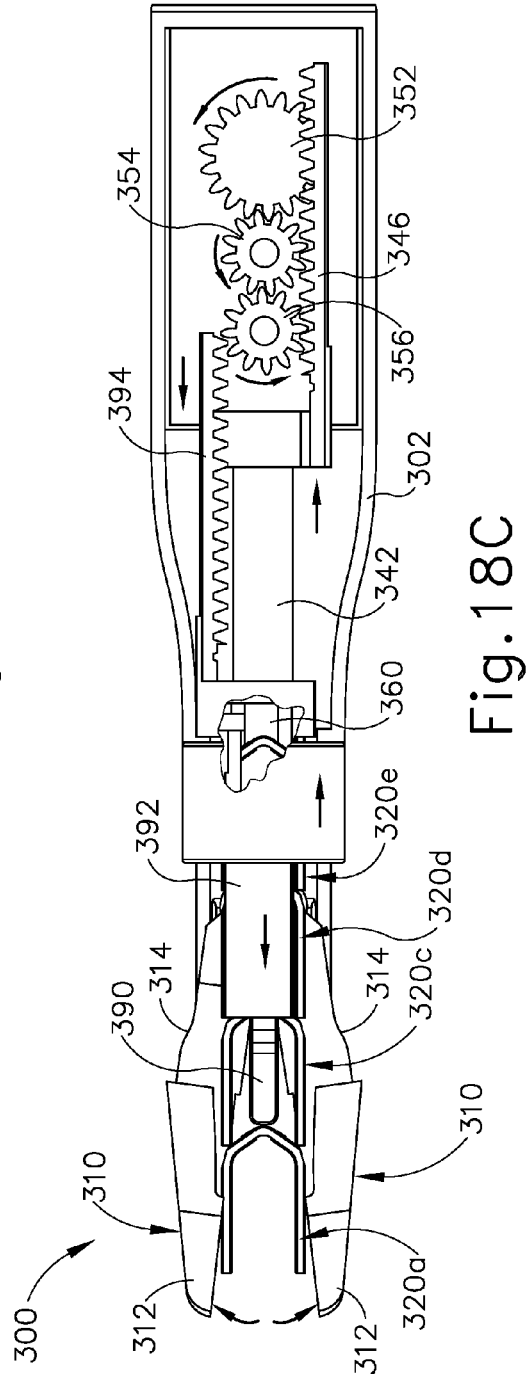
Fig.18B
Fig.18C

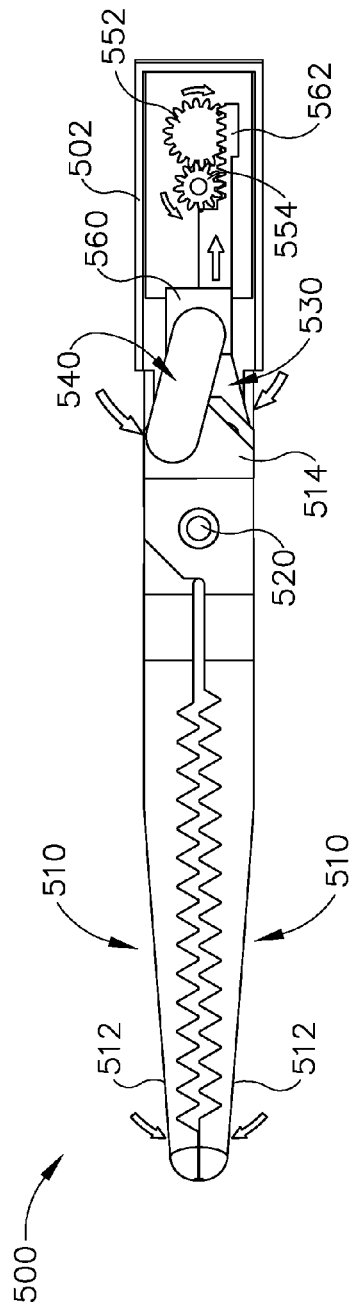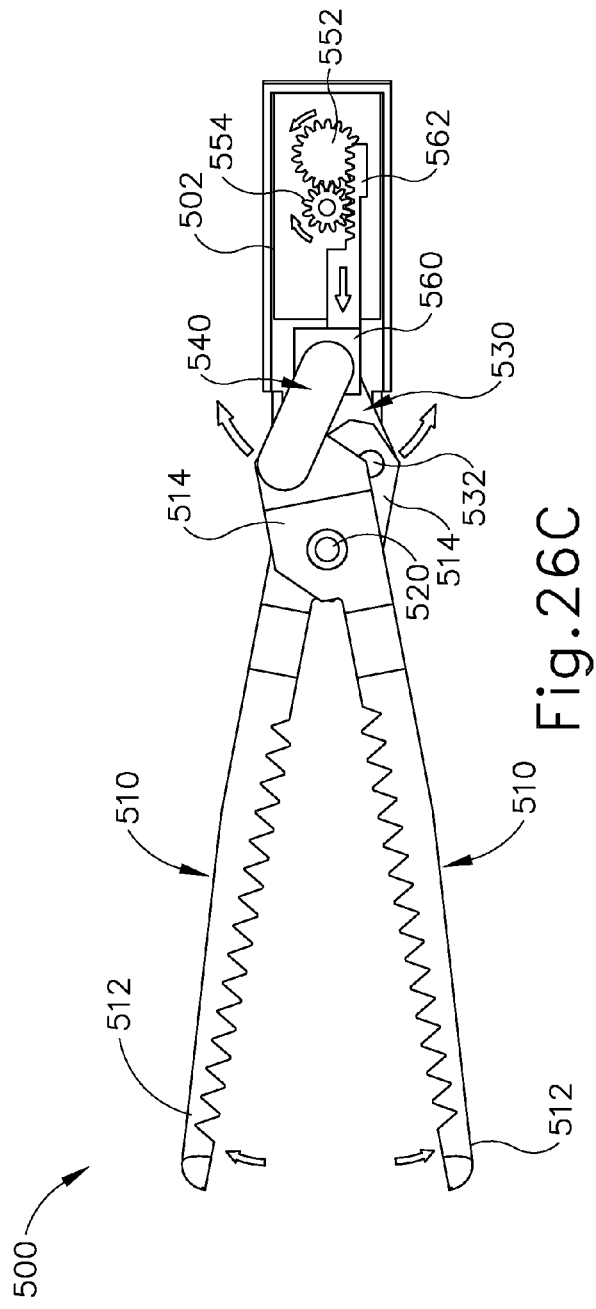

SUTURING INSTRUMENT WITH MULTI-MODE CARTRIDGES

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, now U.S. Pat. No. 9,168,037, issued on Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued on Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, now U.S. Pat. No. 9,474,522, issued on Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 14B depicts a top cross-sectional view of the cartridge of FIG. 11, with the first clip being clamped by the jaws;

FIG. 14C depicts a top cross-sectional view of the cartridge of FIG. 11, with a second clip positioned for clamping by the jaws;

FIG. 18B depicts a top cross-sectional view of the cartridge of FIG. 15, with a portion of an actuation collar broken away to reveal internal components, and with the first clip being clamped by the jaws;

FIG. 18C depicts a top cross-sectional view of the cartridge of FIG. 15, with a portion of an actuation collar and rack member broken away to reveal internal components, and with a second clip positioned for clamping by the jaws;

FIG. 26B depicts a top cross-sectional view of the cartridge of FIG. 23, with the jaws driven from the open state to a closed state;

FIG. 26C depicts a top cross-sectional view of the cartridge of FIG. 23, with the jaws driven from the closed state back to the open state;

Figure 1:
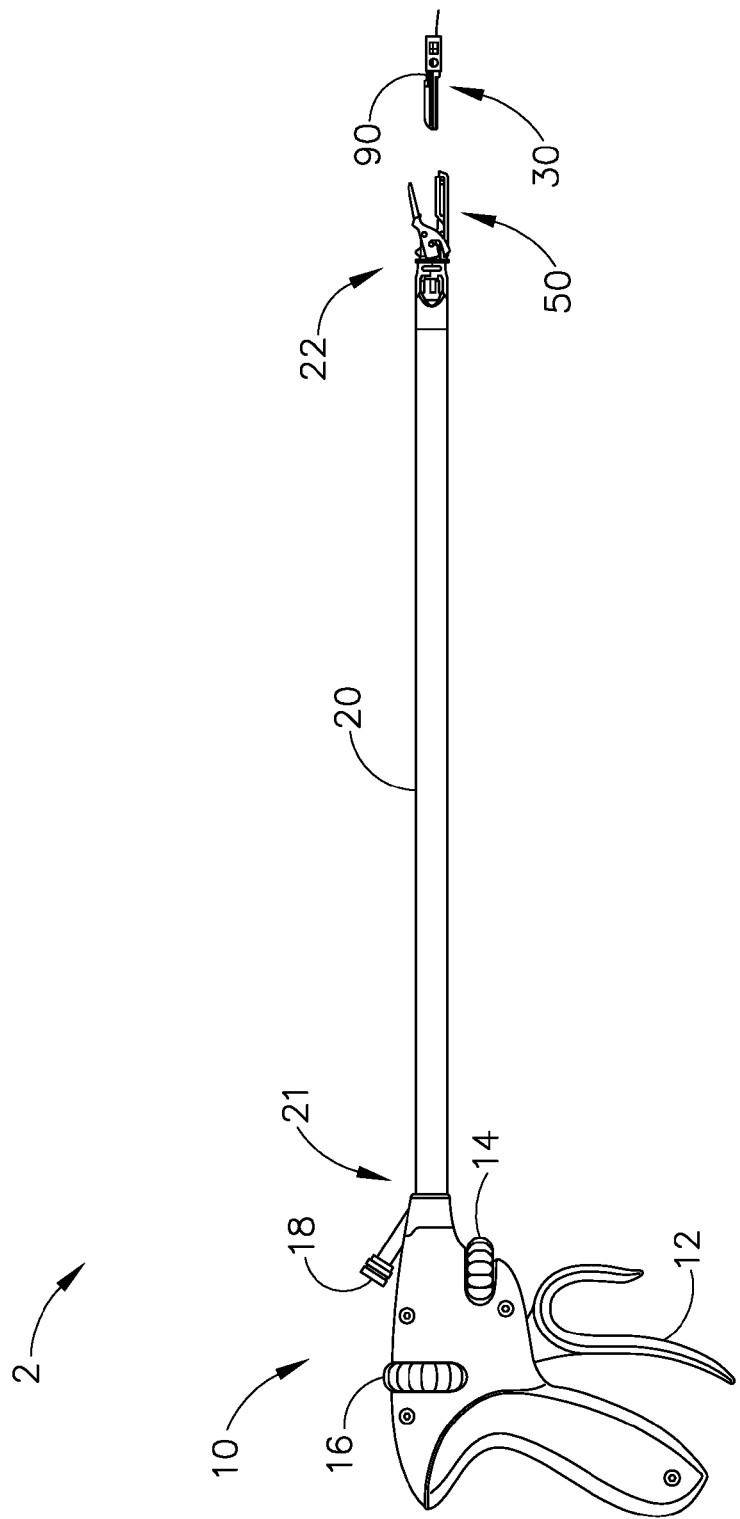
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
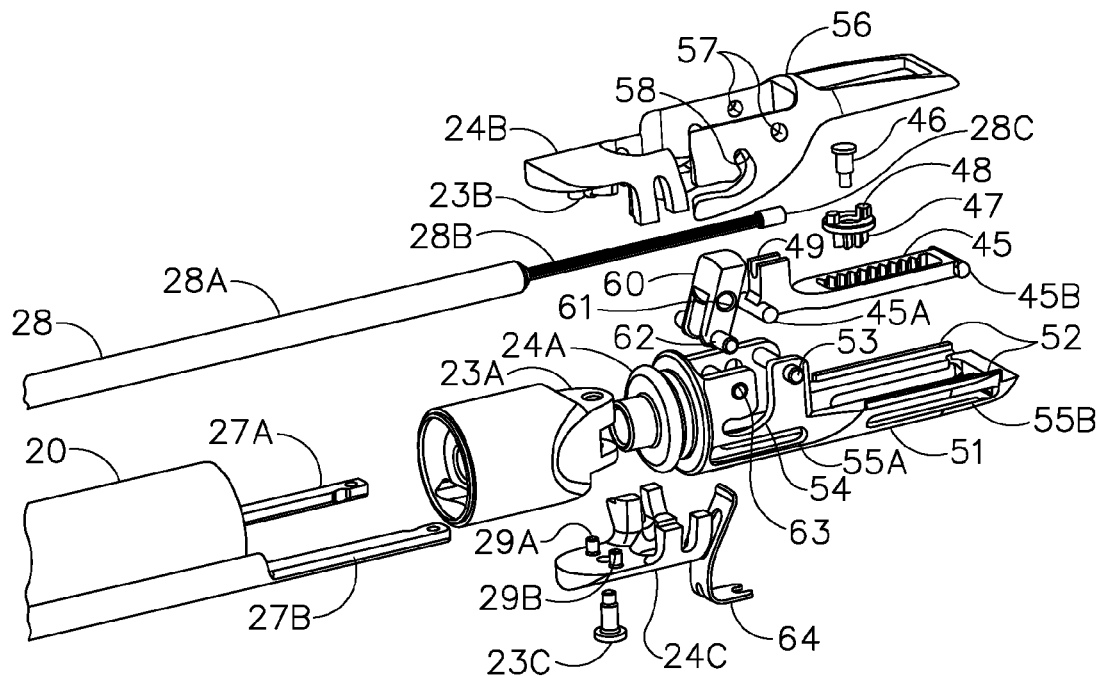
FIG. 2A depicts top perspective exploded view of a cartridge receiving assembly of the instrument of FIG. 1.
Figure 2B:
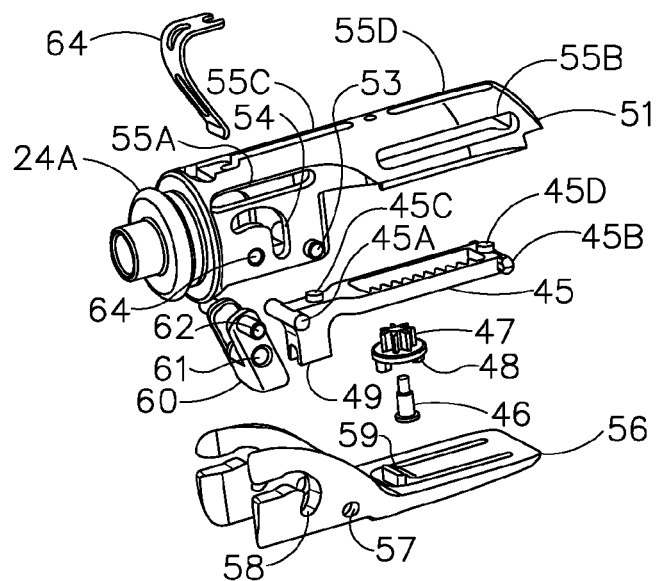
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
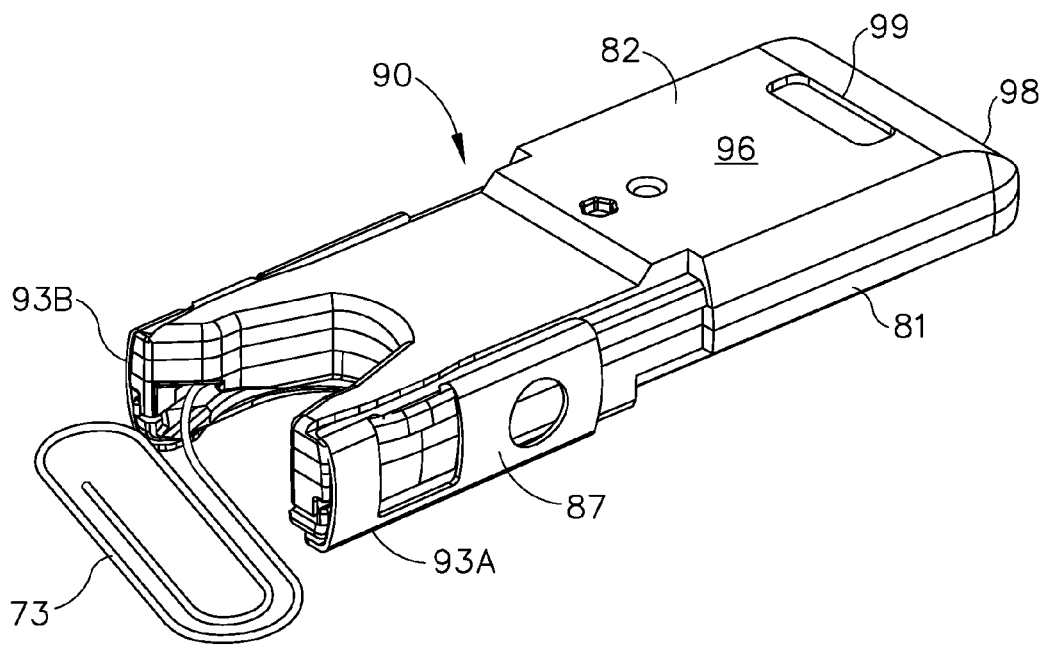
FIG. 3A depicts a top perspective view of an exemplary cartridge configured for receipt in the cartridge receiving assembly of FIG. 2A.
Figure 3B:
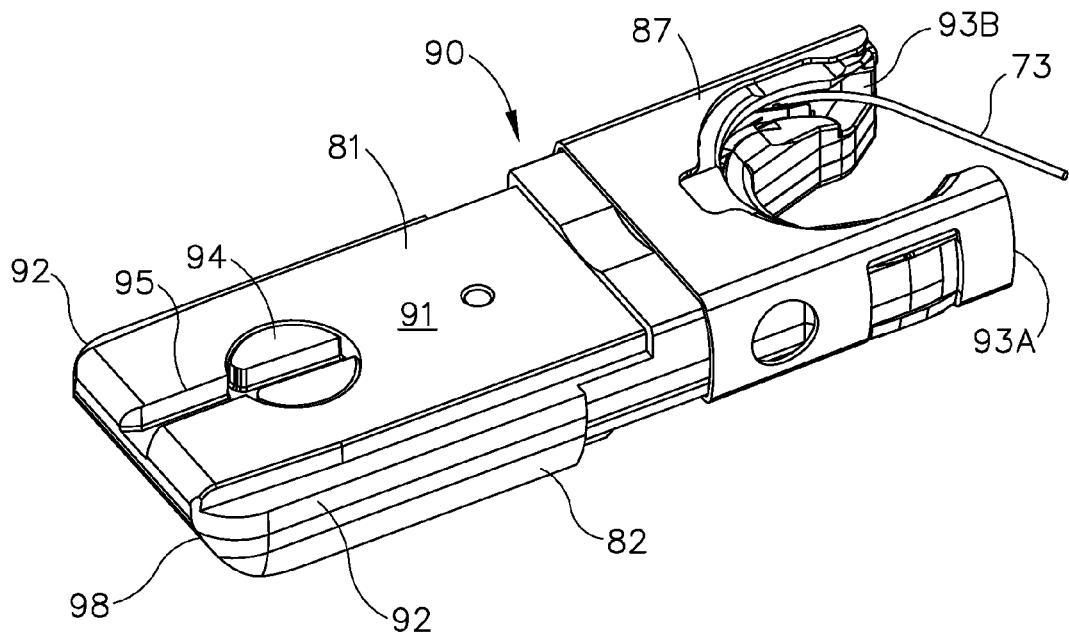
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
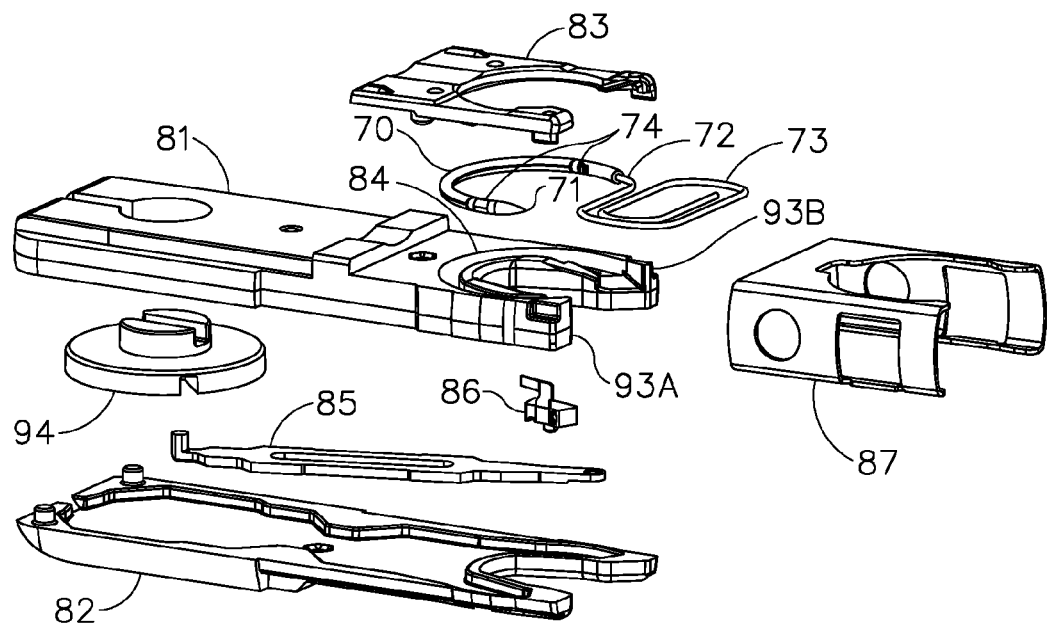
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
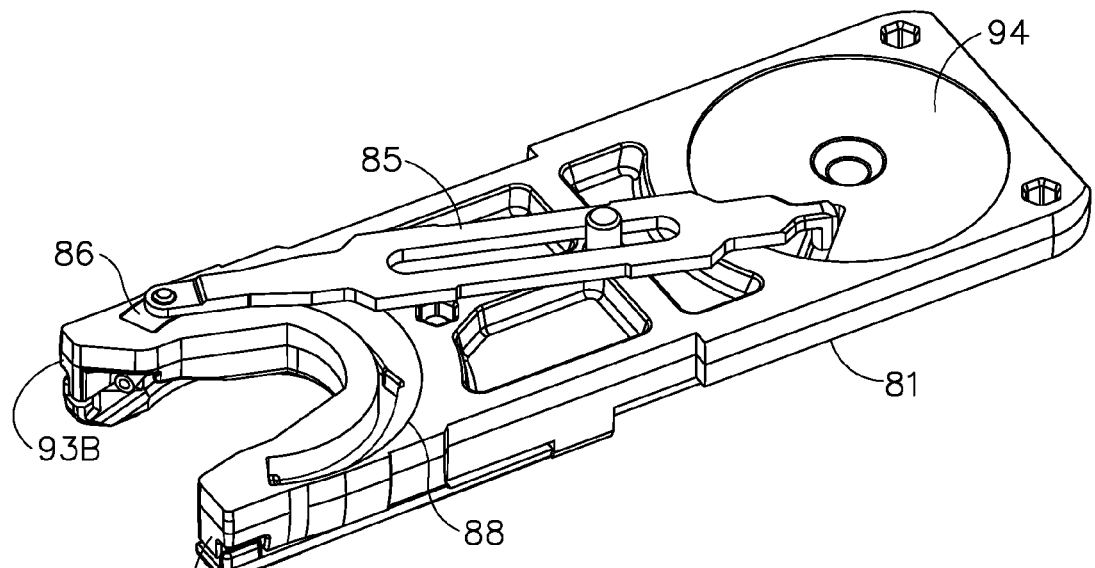
FIG. 5A depicts a perspective view of a drive assembly of the cartridge of FIG. 3A, with the drive assembly at one end of its stroke.
Figure 5B:
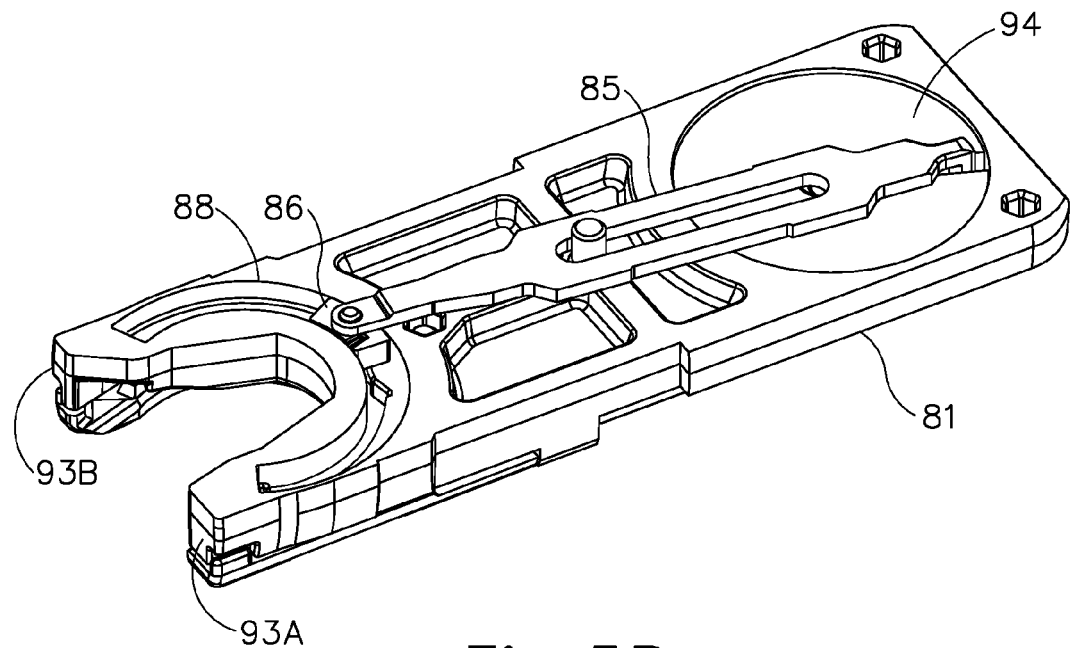
FIG. 5B depicts a perspective view of the drive assembly of FIG. 5A, with the drive assembly at mid-stroke.
Figure 5C:
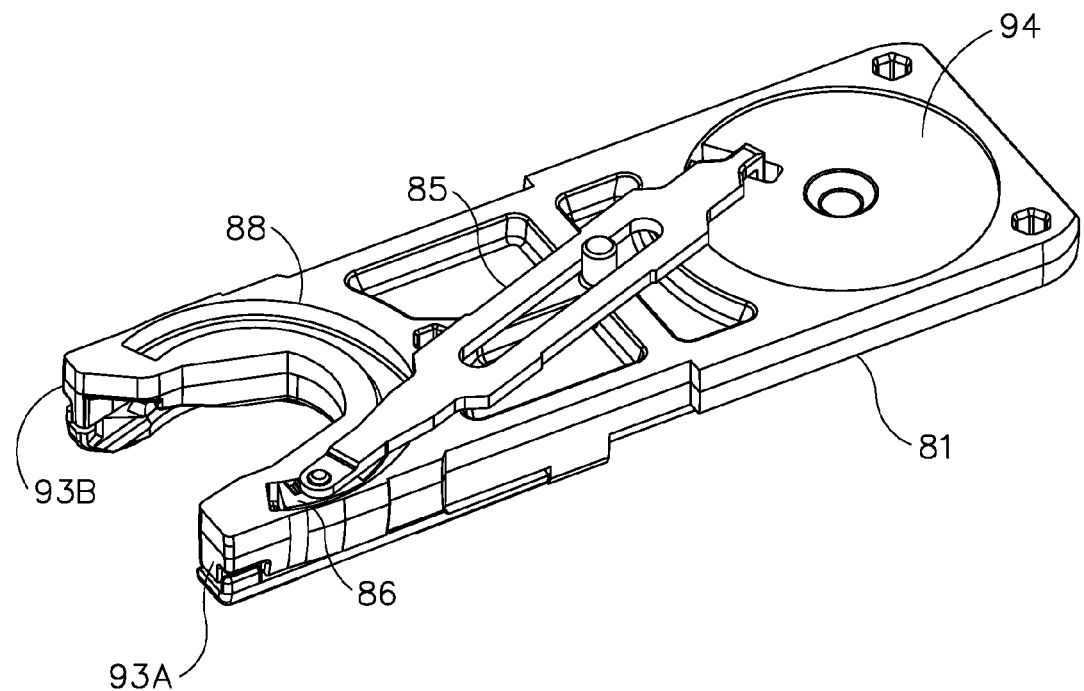
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
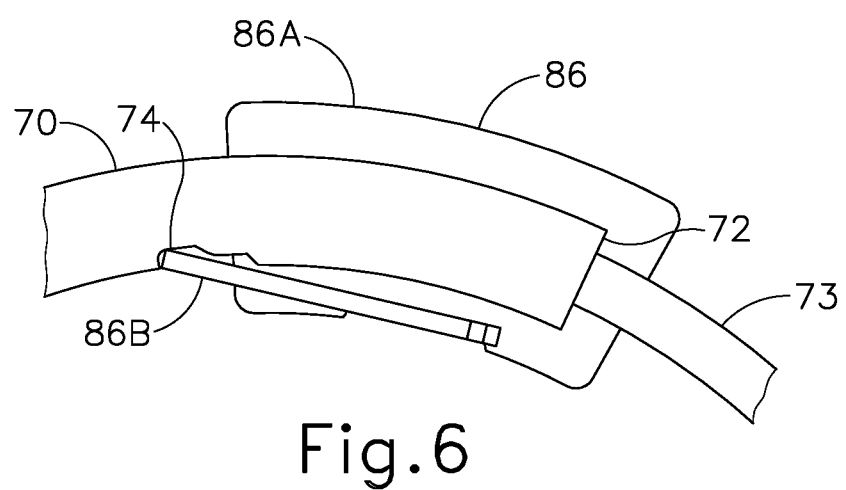
FIG. 6 depicts a partial plan view of a needle driver of the cartridge of FIG. 3A engaging a needle of the cartridge of FIG. 3A.
Figure 7:
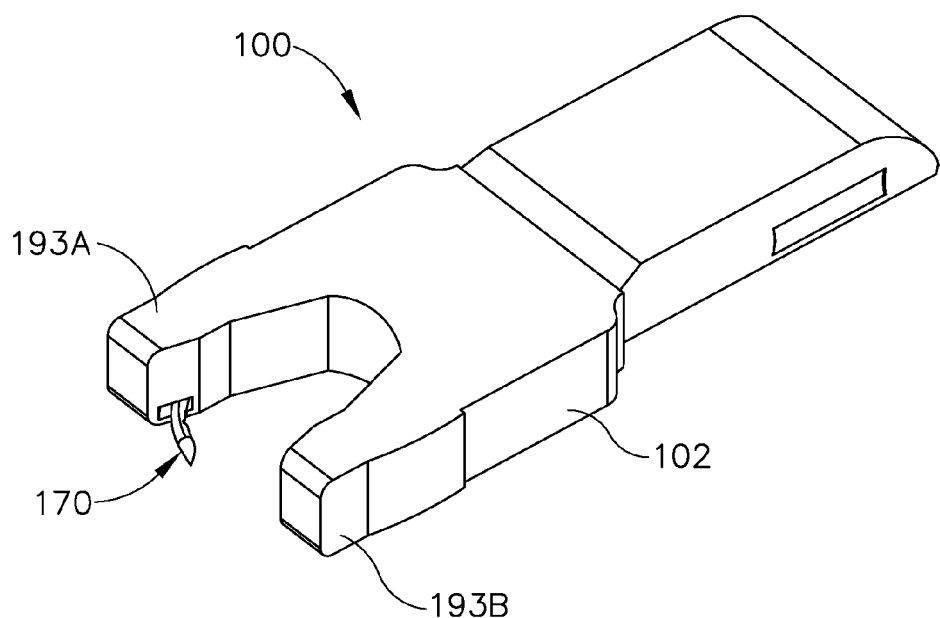
FIG. 7 depicts a perspective view of an exemplary alternative cartridge that may be used with the instrument of FIG. 1.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Figure 8:
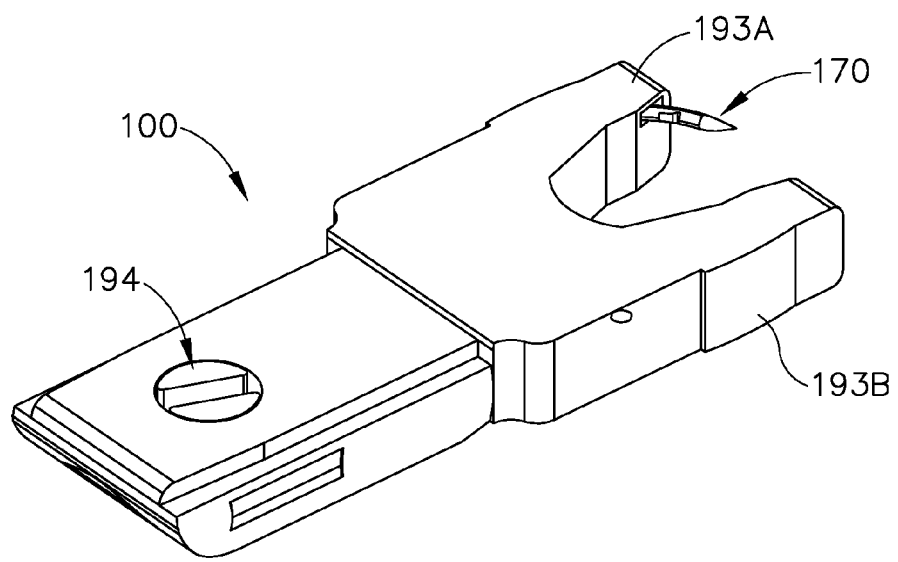
FIG. 8 depicts another perspective view of the cartridge of FIG. 7.

Rotary knob (14) is operable to selectively articulate joint (23). Rotary knob (14) rotates in a plane spaced below and generally parallel with shaft (20). An axle (121) connects rotary knob (14) to a disk (120) in shroud (11) that also rotates in a plane generally parallel with the shaft (20). As shown in FIG. 8, disk (120) comprises first and second cam slots (122A, 122B), each having a length with angular and radial components. In this embodiment, the cam slots (122A, 122B) are two identical spirals offset 180 degrees from one another. Each cam slot (122A, 122B) has an angular span between about 220 degrees and about 300 degrees, with their angular spans overlapping one another. Cam slots (122A, 122B) also increase their distance from the center of disk (120) in the same angular direction. Each cam slot (122A, 122B) has a radial span of about 0.100 inches and about 0.155 inches. Of course, the configuration and dimensions of cam slots (122A, 122B) may alternatively differ from the foregoing.

Figure 11:
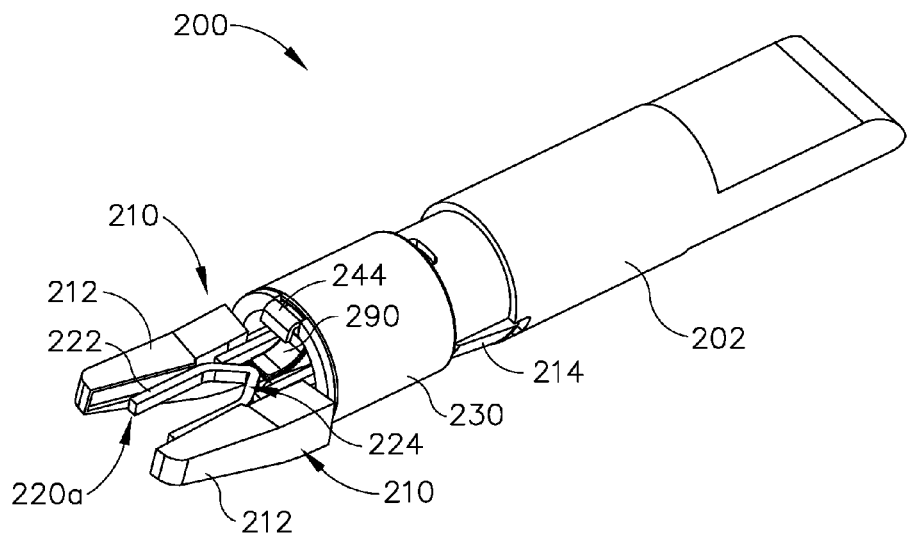
FIG. 11 depicts a perspective view of another exemplary alternative cartridge that may be used with the instrument of FIG. 1.

Cam slot (122A) receives a cam follower (124A) on a distal half of disk (120), and cam slot (122B) receives a cam follower (124B) on the proximal half of disk (120). Followers (124A, 124B) extend downwardly and generally normal from the proximal ends of rods (27A, 27B), respectively. In this example, followers (124A, 124B) are medially offset from longitudinal axes of the respective drive rod (27A, 27B). Rods (27A, 27B) are constrained to slide axially, so counterclockwise rotation of disk (120) moves rod (27B) proximally and simultaneously moves rod (27A) distally to articulate joint (23) to the left of the longitudinal axis (LA) of shaft (20), as shown in the transition from FIG. 11A to FIG. 11B. Similarly, clockwise rotation of disk (120) moves rod (27B) distally and simultaneously moves rod (27A) proximally, thereby articulating joint (23) to the right of the longitudinal axis (LA) of shaft (20), as shown in the transition from FIG. 11A to FIG. 11C.

Cam slots (122A, 122B) each define a tangent axis (126A, 126B) where cam slot (122A, 122B) is engaged by the respective cam followers (124A, 124B). The tangent axes (126A, 126B) may be substantially normal to the longitudinal axes of rods (27A, 27B) so axial push and pull loads on rods (27A, 27B) introduced by side loads on cartridge receiving assembly (50) will not cause disk (120) to rotate. Accordingly, joint (23) will remain locked at its articulated angle. Frictional interfaces or detents may be added to further prevent unintentional articulation, such as between followers (124A, 124B) and cam slots (122A, 122B), between disk (120) and shroud (11), between axle (121) and shroud (11), and/or in any other suitable fashion.

Figure 9:
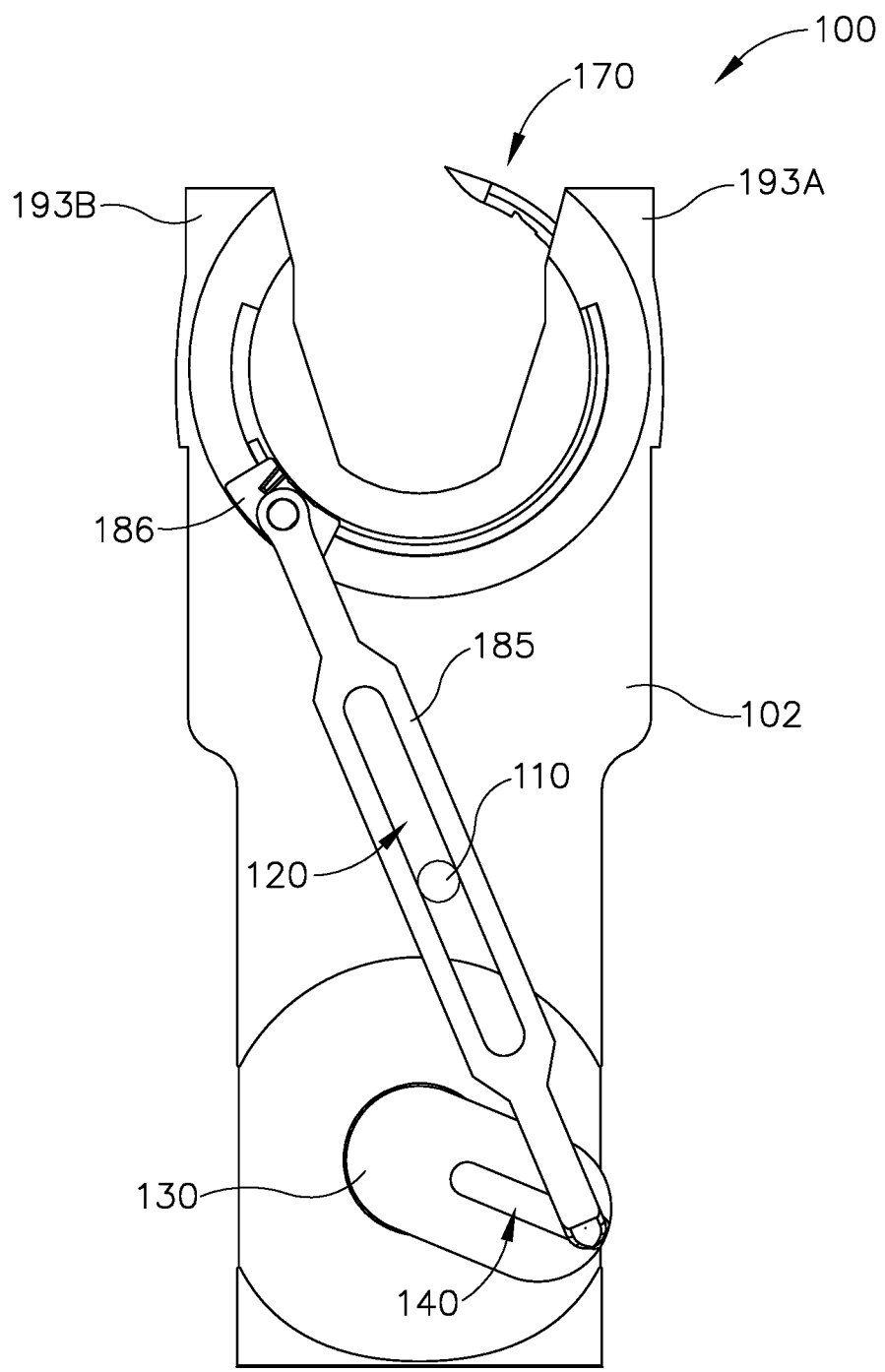
FIG. 9 depicts a top plan view of the cartridge of FIG. 7, with a housing of the cartridge shown in cross-section.

FIG. 9 illustrates an alternative example of an articulation control. A plurality of detents (125) are positioned along cam slots (122A, 122B). In addition to preventing unintentional articulation, detents (125) may provide feedback to the surgeon indicating various angular positions of needle applier cartridge (30) relative shaft (20). Detents (125) may be indexed to correspond to one or more predetermined articulation angles, such as 0 degrees, 15 degrees, 45 degrees, and the like; or detents (125) may be equally distributed along cam slots (122A, 122B). Larger detents (127) may be located at the ends of the cam slots (122A, 122B).

Figure 10:
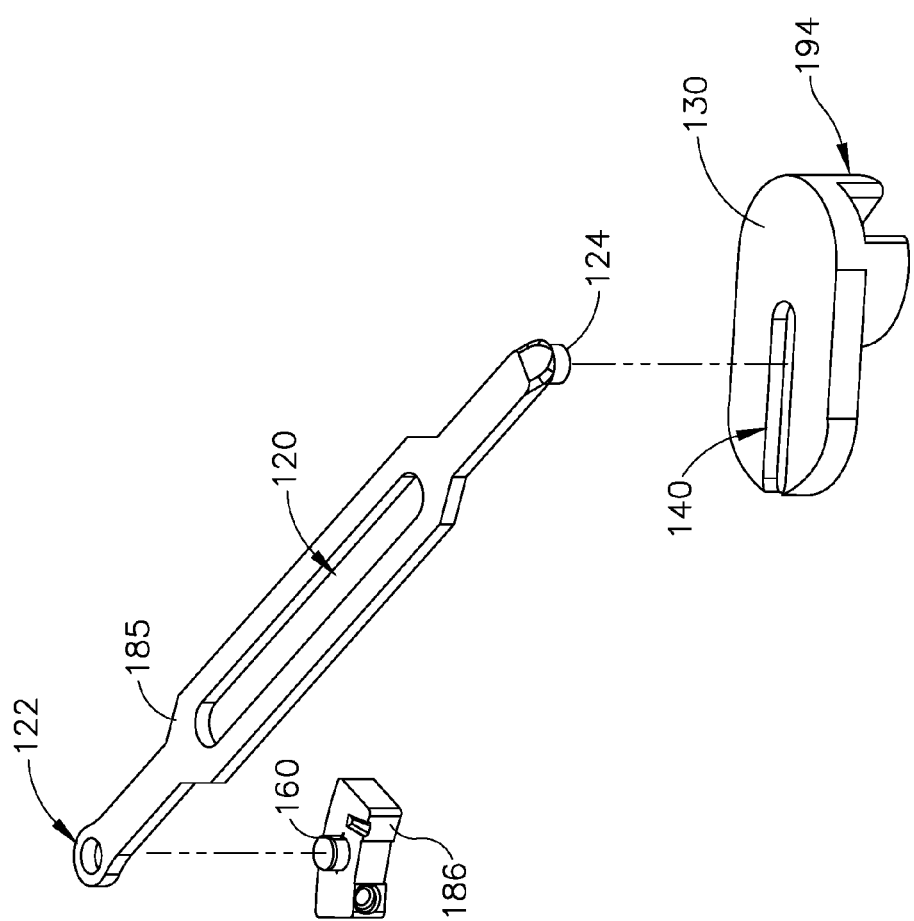
FIG. 10 depicts an exploded perspective view of needle drive components of the cartridge of FIG. 7.

Detents (125) open to the top surface of disk (120), but only partially extend into cam slots (122A, 122B). As shown in FIG. 10, follower (124) extends downwardly from articulation rod (27). Follower (124) includes a straight portion (124C) that closely fits in cam slots (122A, 122B) and a radius portion (124D) dimensioned to be received by detents (125). As disk (120) rotates, radius portion (124D) will raise and lower into detents (125) but the straight portion (124C) will follow and remain engaged in the cam slots (122A, B). In some versions, rod (27) will be biased downwardly toward disk (120) to provide a tactile and/or audible "click" as radius portion (124D) engages detents (125).

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued on Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat. No. 9,474,522, issued on Oct. 25, 2016, the disclosure of which is incorporated by reference herein; and U.S. patent application Ser. No. 14/298,038, entitled "Circular Needle Applier with Cleats," filed Jan. 30, 2015, now. U.S. Pat. No. 9,375,212, issued on Jun. 28, 2016, the disclosure of which is incorporated by reference herein. It should be understood that such details, explanations, examples, and alternative embodiments may be readily applied to the above-described instrument (10) and subcomponents thereof.

II. Exemplary Alternative Cartridges

In some instances, it may be desirable to use different cartridges with instrument (10) to perform different surgical functions. For instance, it may be desirable to use an alternative cartridge with instrument (10) in order to perform a suturing operation with a needle having a greater length and radius of curvature than needle (70). As another example, it may be desirable to use an alternative cartridge with instrument (10) in order to apply malleable surgical clips at a surgical site. As another example, it may be desirable to use an alternative cartridge with instrument (10) in order to apply an anchor clip to a suture (73) after suture (73) has been passed through tissue to form one or more stitches, to prevent suture (73) from undesirably pulling through the tissue and compromising the one or more stitches. As another example, it may be desirable to use an alternative cartridge with instrument (10) in order to grasp or sever tissue and/or other items within a patient. As another example, it may be desirable to use an alternative cartridge with instrument (10) in order to apply staples to tissue in a patient. These various kinds of operating modalities may be selected based on the particular surgical procedure at hand. Moreover, an operator may use different cartridges providing different kinds of operating modalities with the same instrument (10) in a single surgical procedure. For instance, if one stage of the surgical procedure calls for suturing, the operator may secure a suturing cartridge to instrument (10). If another stage of the same surgical procedure calls for stapling, the operator may remove the suturing cartridge from instrument (10) and secure a stapling cartridge to instrument (10).

The configuration of cartridge receiving assembly (50) lends itself to accepting various kinds of cartridges that provide various kinds of operating modalities such as those noted above, provided that the modular cartridges are configured to fit in cartridge receiving assembly (50) and are operable to receive a rotary drive input from key (48) of cartridge receiving assembly (50). The following description relates to various examples of modular cartridges that may be received in cartridge receiving assembly (50) and that may thereby convert a rotary drive input from key (48) into an actuation motion. It should therefore be understood that each of the exemplary cartridges described below may be driven in response to actuation of first input (12). It should also be understood that the following cartridges are just merely illustrative examples. Other examples will be apparent to those of ordinary skill in the art in view of the teachings herein.

A. Exemplary Cartridge with Large Needle

FIGS. 7-10 show another exemplary cartridge (100) that may be readily used with instrument (10). In particular, cartridge (100) is configured to be removably received in cartridge receiving assembly (50). It should be understood that cartridge (100) may be selectively secured in and released from cartridge receiving assembly (50) in the same manner in which cartridge (30) is selectively secured in and released from cartridge receiving assembly (50) as described above. Cartridge (100) includes a housing (102) and a rotary input (194). As best seen in FIG. 8, rotary input (194) includes a slot that is configured to mate with key (48) of cartridge receiving assembly (50), such that cartridge (100) is actuated by rotation of key (48) as will be described in greater detail below. It should therefore be understood that cartridge (100) is actuated by actuation of first input (12). As will also be described in greater detail below, cartridge (100) will drive a needle (170) from a first arm (193A) to a second arm (193B) when cartridge (100) is actuated by first input (12).

As shown in FIGS. 9-10, cartridge (100) includes an integral needle (170), a needle driver (186), a drive link (185), and a rotary cam (130). Needle (170) is configured just like needle (70), except that needle (170) of this example has a larger radius of curvature than needle (70) and is longer than needle (70). By way of example only, needle (170) may extend along an arc having a radius of curvature (along the centerline of needle (170)) of approximately 0.325 inches and a length of approximately 1.355; while needle (70) may extend along an arc having a radius of curvature (along the centerline of needle (70)) of approximately 0.196 inches and a length of approximately 0.826 inches. As another merely illustrative example, either needle (70, 170) may have a radius of curvature (along the centerline of needle (70, 170)) of approximately 0.275 inches and a length of approximately 1.151 inches. Of course, these values are merely illustrative examples. Needles (70, 170) may instead have any other sizes.

Needle driver (186) and drive link (185) are configured to operate substantially identically to needle driver (86) and link (85) described above, though it should be understood that needle driver (186) and link (85) drive needle (170) along an orbital path having a larger radius than the orbital path of needle (70). As best seen in FIG. 10, link (185) includes a distal opening (122) that pivotably receives an integral post of needle driver (186). Link (185) further includes an integral post (124) that is slidably disposed within a cam slot (140) of rotary cam (130). As is also shown in FIG. 10, rotary cam (130) is an integral feature of rotary input (194). It should therefore be understood that rotation of rotary input (194) will cause cam slot (140) to rotate about a central axis of rotary input (194). As best seen in FIG. 9, link (185) also includes an elongate slot (120) that slidably receives an integral post (110) of housing (102).

It should be understood that rotary oscillation of rotary input (194) will cause link (185) to move in a manner similar to that shown in FIGS. 5A-5C and described above with respect to link (85). This movement of link (185) will be driven by the engagement of post (124) in slot (140) and will be guided by post (110) in slot (120). This movement of link (185) will result in orbital oscillation of needle driver (186), and thus orbital motion of needle (170), as described above with reference to FIGS. 5A-5C in the context of driver (86) and needle (70). Cartridge (100) of this example thus operates substantially similarly to cartridge (30). However, the larger size of needle (170) and the wider spacing of arms (193A, 193B) allow cartridge (100) to be used with tissue thicknesses that are greater than those accommodated by cartridge (30). An operator may thus choose cartridge (30) when a particular surgical procedure (or particular stage within a surgical procedure) calls for suturing tissue with a relatively small thickness; and choose cartridge (100) when a particular surgical procedure (or particular stage within a surgical procedure) calls for suturing tissue with a relatively large thickness. As noted above, the operator may even use both kinds of cartridges (30, 100) with the same instrument (10) at different stages of the same surgical procedure. Other suitable ways in which cartridge (100) may be modified and used will be apparent to those of ordinary skill in the art in view of the teachings herein.

B. Exemplary Cartridge with Malleable Surgical Clips and Single Rack Drive

Figure 12:
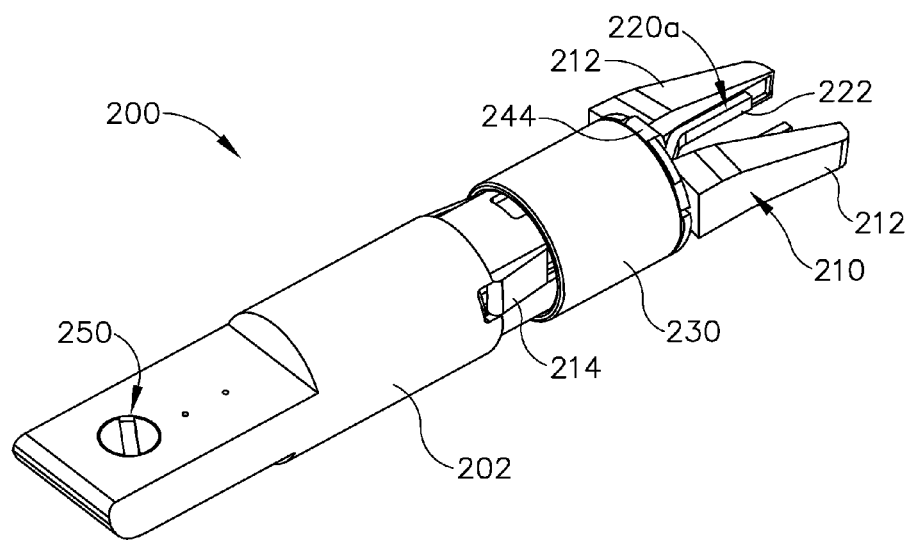
FIG. 12 depicts another perspective view of the cartridge of FIG. 11.

FIGS. 11-14C show another exemplary cartridge (200) that may be readily used with instrument (10). In particular, cartridge (200) is configured to be removably received in cartridge receiving assembly (50). It should be understood that cartridge (200) may be selectively secured in and released from cartridge receiving assembly (50) in the same manner in which cartridge (30) is selectively secured in and released from cartridge receiving assembly (50) as described above. Cartridge (200) includes a housing (202) and a rotary input (250). As best seen in FIG. 12, rotary input (250) includes a slot that is configured to mate with key (48) of cartridge receiving assembly (50), such that cartridge (200) is actuated by rotation of key (48) as will be described in greater detail below. It should therefore be understood that cartridge (200) is actuated by actuation of first input (12). As will also be described in greater detail below, cartridge (200) will apply a surgical clip (220) to tissue when cartridge (200) is actuated by first input (12).

Cartridge (200) is configured to provide instrument (10) with functionality similar to that of a LIGAMAX™ instrument by Ethicon Endo-Surgery, Inc. of Cincinnati, Ohio. In particular, cartridge (200) is operable to apply a selected number of surgical clips (220) to tissue, such as to ligate a vessel within the patient and/or for any other suitable purpose(s). Each clip (220) of the present example has a pair of legs (222) and a crown portion (224), providing each clip (220) with a "U" shape. As will be described in greater detail below, each clip (220) may be deformed by urging legs (222) toward each other. The material forming clip (220) is malleable such that clip (220) will maintain the deformed configuration. Clip (220) is thus suitable for ligating vessels that are captured between legs (222). By way of example only, clip (220) may be constructed and operable in accordance with at least some of the teachings of U.S. Pat. No. 7,699,860, entitled "Surgical Clip," issued Apr. 20, 2010, the disclosure of which is incorporated by reference herein. Alternatively, clip (220) may have any other suitable configuration.

Figure 13:
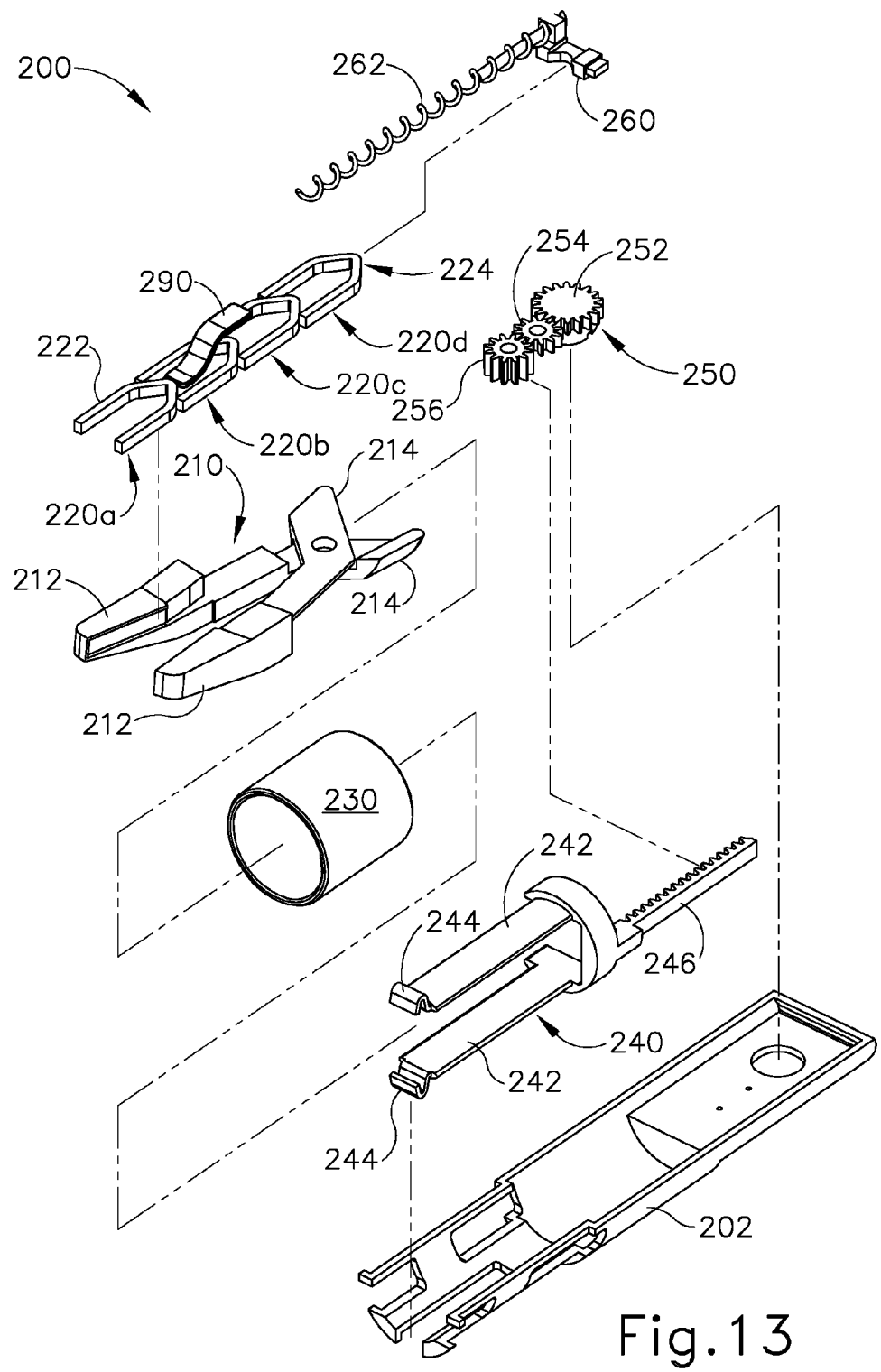
FIG. 13 depicts an exploded perspective view of the cartridge of FIG. 11, with a housing of the cartridge shown in cross-section.
Figure 14A:
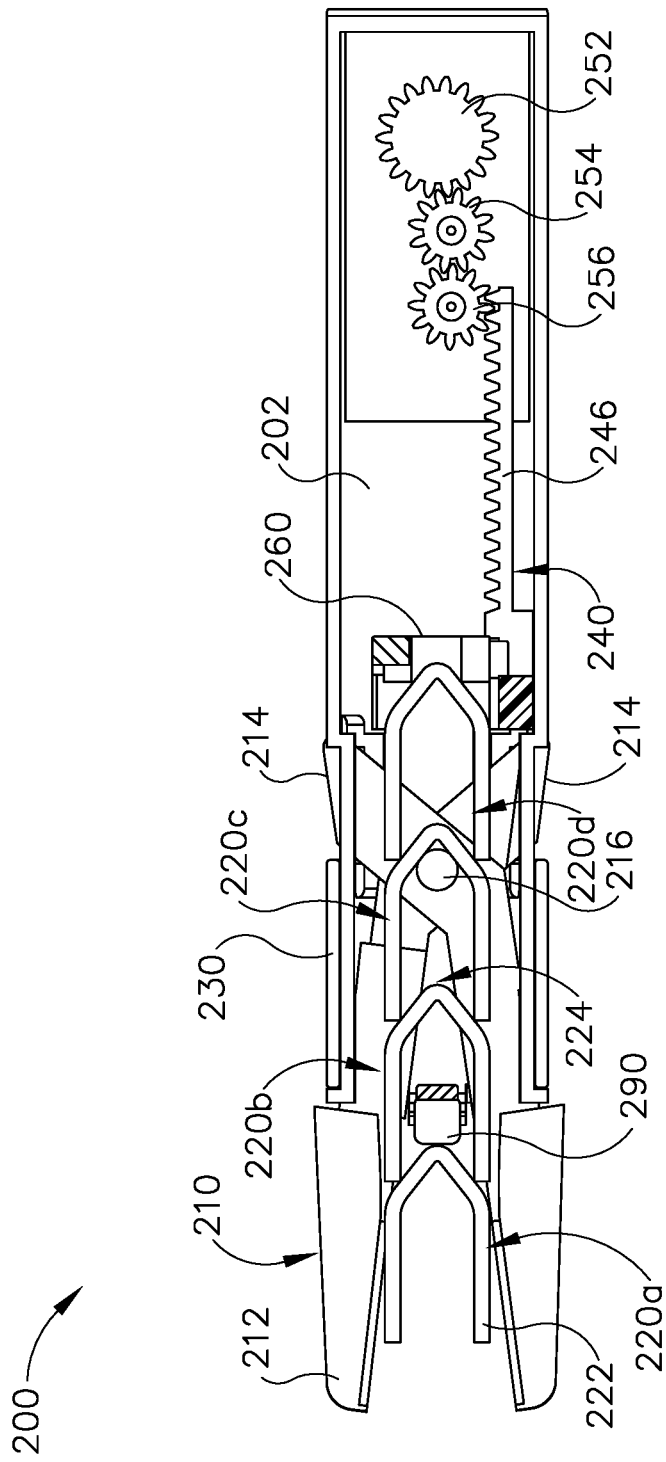
FIG. 14A depicts a top cross-sectional view of the cartridge of FIG. 11, with a first clip positioned for clamping by jaws of the cartridge.
Figure 15:
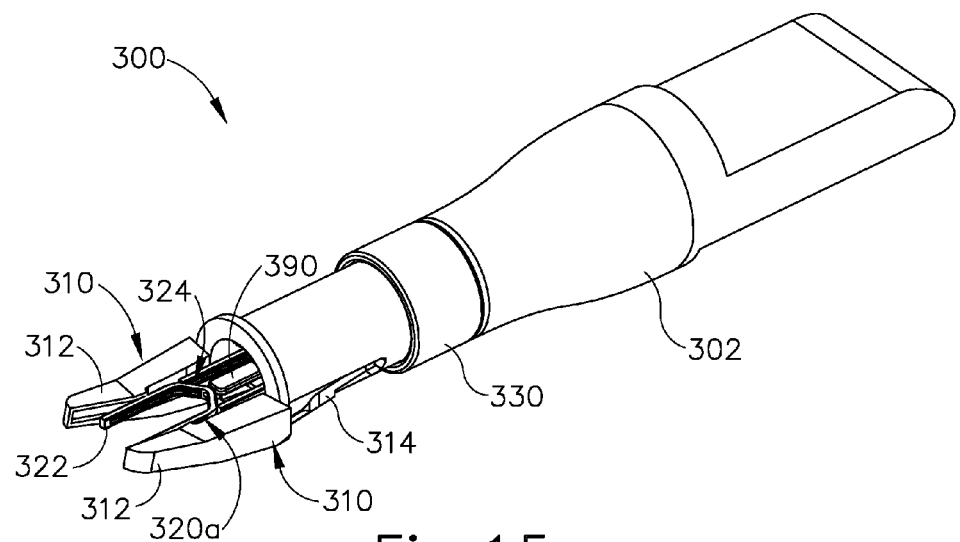
FIG. 15 depicts a perspective view of another exemplary alternative cartridge that may be used with the instrument of FIG. 1.

Cartridge (200) of the present example is operable to deform clip (220) by actuating a pair of jaws (210), which extend distally from housing (202). As best seen in FIG. 13, each jaw (210) has a distal end (212) and a proximal end (214). Jaws (210) overlap with each other and are pivotably secured together by a pin (216), which is located between ends (212, 214) as shown in FIGS. 14A-14C. Jaws (210) are actuated by an actuation collar (230), which is driven by a driver (240). Collar (230) is slidably disposed about the exterior of housing (202) and is operable to move between a distal position and a proximal position as will be described in greater detail below. As best seen in FIG. 13, driver (240) comprises a pair of distally projecting arms (242), each arm (242) having a respective coupling feature (244) that couples driver (240) with collar (230). Driver (240) also includes a proximally projecting rack (246).

Rack (246) has teeth that mesh with teeth of a pinion gear (256), which is rotatably supported in housing (202). The teeth of pinion gear (256) mesh with the teeth of an idler gear (254), which is also rotatably supported in housing (202). The teeth of idler gear (254) mesh with the teeth of a drive gear (252), which is also rotatably supported in housing (202). Drive gear (252) is an integral feature of rotary input (250). It should therefore be understood that when key (48) rotates rotary input (250), such rotation will ultimately be communicated to pinion gear (256) via gears (252, 254). It should also be understood that rotation of pinion gear (256) will cause longitudinal translation of rack (246), which will in turn cause longitudinal translation of collar (230). As will be described in greater detail below, this longitudinal translation of collar (230) will transition jaws (210) between an open state and a closed state.

In the present example, pinion gear (256) is taller than gears (252, 254). Rack (246) engages pinion gear (256) at an upper section of pinion gear (256) while idler gear (254) engages pinion gear (256) at a lower section of pinion gear (256). Drive gear (252) is located at the same vertical position as idler gear (254) such that the vertical position of drive gear (252) corresponds with the lower section of pinion gear (256). This vertical arrangement of gears (252, 254, 256) enables rack (246) to pass above gears (252, 254), without engaging gears (252, 254), as rack (246) translates to a proximal position. Of course, gears (252, 254, 256) may instead be positioned in any other suitable arrangement that enables rack (246) to translate longitudinally without engaging gears (252, 254).

In the present example, cartridge (200) houses four surgical clips (220a, 220b, 220c, 220d). Alternatively, cartridge (200) may house any other suitable number of clips (220). As best seen in FIG. 13, cartridge (200) includes a biasing saddle (260) coupled with a resilient member (262). Resilient member (262) is further engaged with housing (202) and is configured to resiliently urge biasing saddle (260) distally. Biasing saddle (260) is configured to engage the proximal-most clip (220d) and thereby urge the proximal-most clip (220d) distally. Clips (220a, 220b, 220c, 220d) are arranged to contact each other in a line such that the distal bias provided to clip (220d) is further provided to the rest of clips (220a, 220b, 220c).

Cartridge (200) further includes a retainer (290) that is configured to selectively retain clips (220) in housing (202). Retainer (290) comprises a dogleg-shaped leaf spring. A proximal end of retainer (290) is fixedly secured to housing (202) while a distal end of retainer (290) is positioned to engage crown (224) of the distal-most clip (220a). In some versions, retainer (290) prevents the distal-most clip (220a) from traveling distally while jaws (210) are in the open configuration, despite the distal bias imparted by resilient member (262) and saddle (260). In addition or in the alternative, retainer (290) prevents the distal-most clip (220a) from traveling proximally while jaws (210) are in the open position. It should also be understood that jaws (210) may include features that prevent the resilient bias of biasing saddle (260) and resilient member (262) from prematurely ejecting the distal-most clip (220a) from jaws (210). Various suitable ways in which clips (220) may be selectively retained in cartridge (200) will be apparent to those of ordinary skill in the art in view of the teachings herein.

FIGS. 14A-14C show cartridge (200) at various stages of operation. In particular, FIG. 14A shows cartridge (200) in a pre-actuated state where distal-most clip (220a) is positioned between open jaws (210). In this state, the proximal ends (214) of jaws (210) protrude outwardly from housing (202). Actuation collar (230) is positioned distally, distal to the protruding proximal ends (214) of jaws (210). Cartridge (200) may be loaded in cartridge receiving assembly (50) while cartridge (200) is in the pre-actuated state shown in FIG. 14A.

After the operator loads cartridge (200) in cartridge receiving assembly (50), the operator may position cartridge (200) in a location where a vessel or other anatomical structure is positioned between legs (222) of distal-most clip (220a). The operator may then actuate first input (12) to drive rotation of key (48) as described above. This rotation of key (48) in a first angular direction is communicated to rotary input (250), thereby rotating drive gear (252) in the first angular direction as shown in FIG. 14B. This rotation of drive gear (252) is communicated to pinion gear (256) via idler gear (254). The rotation of pinion gear (256) drives rack (246) proximally. The proximal movement of rack (246) drives collar (230) proximally via arms (242) and coupling features (244). As collar (230) moves proximally, collar (230) bears on proximal ends (214) of jaws (210) and thereby drives proximal ends (214) of jaws (210) inwardly. As proximal ends (214) of jaws (210) move inwardly, jaws (210) pivot about pin (216), thereby driving distal ends (212) of jaws (210) toward each other.

As distal ends (212) of jaws (210) pivot toward each other, distal ends (212) urge legs (222) of distal-most clip (220a) toward each other, thereby compressing distal-most clip (220a). As shown in FIG. 14B, legs (222) are compressed against each other in apposition. While not shown in FIG. 14B, it should be understood that a vessel or other anatomical structure may be captured between legs (222) such that legs (222) provide ligation of the vessel or other anatomical structure. The malleable properties of the material forming clip (220) will maintain the compressed configuration until clip (220) is absorbed or otherwise disintegrates.

When the operator releases first input (12), key (48) will rotate in a second angular direction. This rotation of key (48) in a second angular direction is communicated to rotary input (250), thereby rotating drive gear (252) in the second angular direction as shown in FIG. 14C. This rotation of drive gear (252) is communicated to pinion gear (256) via idler gear (254). The rotation of pinion gear (256) drives rack (246) distally. The distal movement of rack (246) drives collar (230) distally via arms (242) and coupling features (244). As collar (230) moves distally, collar (230) disengages proximal ends (214) of jaws (210), allowing proximal ends (214) of jaws (210) to pivot outwardly. As proximal ends (214) of jaws (210) move outwardly, jaws (210) pivot about pin (216), thereby driving distal ends (212) of jaws (210) away from each other.

As distal ends (212) of jaws (210) pivot away from each other, jaws (210) release the deformed distal-most clip (220a). In some versions, a leaf spring, torsion spring, or other kind of resilient member urges jaws (210) toward the open position as soon as collar (230) is translated distally. In some other versions, a camming feature drives jaws (210) toward the open position as collar (230) is translated distally. Various suitable components, features, and configurations that may be used to urge jaws (210) toward the open position as collar (230) is translated distally will be apparent to those of ordinary skill in the art in view of the teachings herein.

In addition to releasing the deformed distal-most clip (220a), and as shown in FIG. 14C, the opened jaws (210) will receive a second clip (220b) that was previously just proximal to distal-most clip (220a). In particular, biasing saddle (260) and resilient member (262) will urge second clip (220b) distally via the other clips (220c, 220d), thereby positioning second clip (220b) between distal ends (212) of jaws (210). In some versions, distal ends (212) of jaws (210) include features that arrest distal movement of second clip (220b) at this stage. In addition or in the alternative, retainer (290) may arrest distal movement of second clip (220b) at this stage. It should be understood that retainer (290) may flex to accommodate distal movement of clip (220a) and/or clip (220b) during the transition from the state shown in FIG. 14B to the state shown in FIG. 14C.

It should be understood from the foregoing that an operator may successively apply each clip (220) in cartridge (200) by repeatedly actuating and releasing first input (12). In the event that all of the clips (220) in cartridge (200) have been used and the operator wishes to apply additional clips (220), the operator may simply remove the spent cartridge (200) from cartridge receiving assembly (50) and secure a new cartridge (200) to cartridge receiving assembly (50). Alternatively, the operator may secure any other cartridge described herein to cartridge receiving assembly (50), such as to perform additional surgical tasks of different modalities.

C. Exemplary Cartridge with Malleable Surgical Clips and Dual Rack Drive

Figure 16:
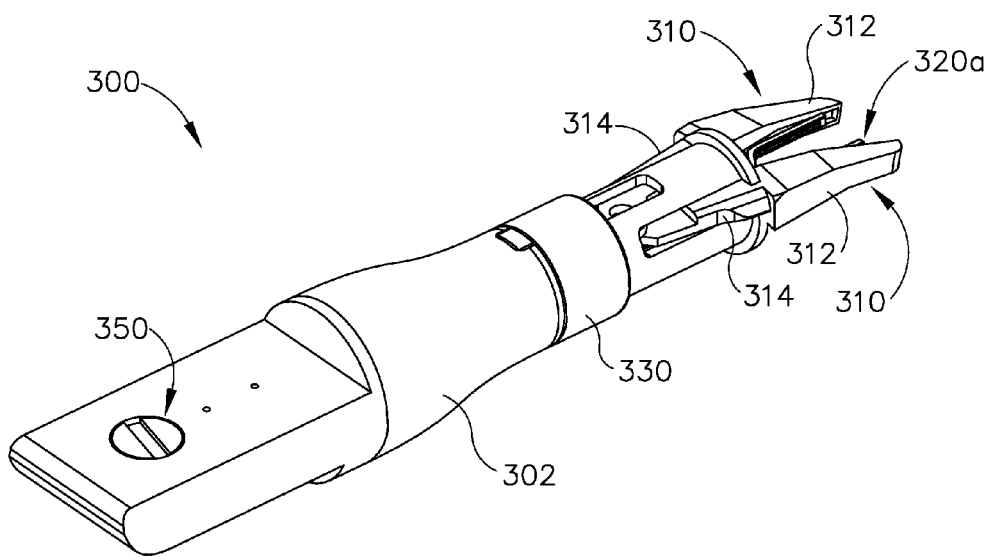
FIG. 16 depicts another perspective view of the cartridge of FIG. 15.

FIGS. 15-18C show another exemplary cartridge (300) that may be readily used with instrument (10). In particular, cartridge (300) is configured to be removably received in cartridge receiving assembly (50). It should be understood that cartridge (300) may be selectively secured in and released from cartridge receiving assembly (50) in the same manner in which cartridge (30) is selectively secured in and released from cartridge receiving assembly (50) as described above. Cartridge (300) includes a housing (302) and a rotary input (350). As best seen in FIG. 16, rotary input (350) includes a slot that is configured to mate with key (48) of cartridge receiving assembly (50), such that cartridge (300) is actuated by rotation of key (48) as will be described in greater detail below. It should therefore be understood that cartridge (300) is actuated by actuation of first input (12). As will also be described in greater detail below, cartridge (300) will apply a surgical clip (320) to tissue when cartridge (300) is actuated by first input (12).

Cartridge (300) is configured to provide instrument (10) with functionality similar to that of a LIGAMAX™ instrument by Ethicon Endo-Surgery, Inc. of Cincinnati, Ohio. In particular, cartridge (300) is operable to apply a selected number of surgical clips (320) to tissue, such as to ligate a vessel within the patient and/or for any other suitable purpose(s). Each clip (320) of the present example has a pair of legs (322) and a crown portion (324), providing each clip (320) with a "U" shape. As will be described in greater detail below, each clip (320) may be deformed by urging legs (322) toward each other. The material forming clip (320) is malleable such that clip (320) will maintain the deformed configuration. Clip (220) is thus suitable for ligating vessels that are captured between legs (322). By way of example only, clip (320) may be constructed and operable in accordance with at least some of the teachings of U.S. Pat. No. 7,699,860, entitled "Surgical Clip," issued Apr. 20, 2010, the disclosure of which is incorporated by reference herein. Alternatively, clip (320) may have any other suitable configuration.

Figure 17:
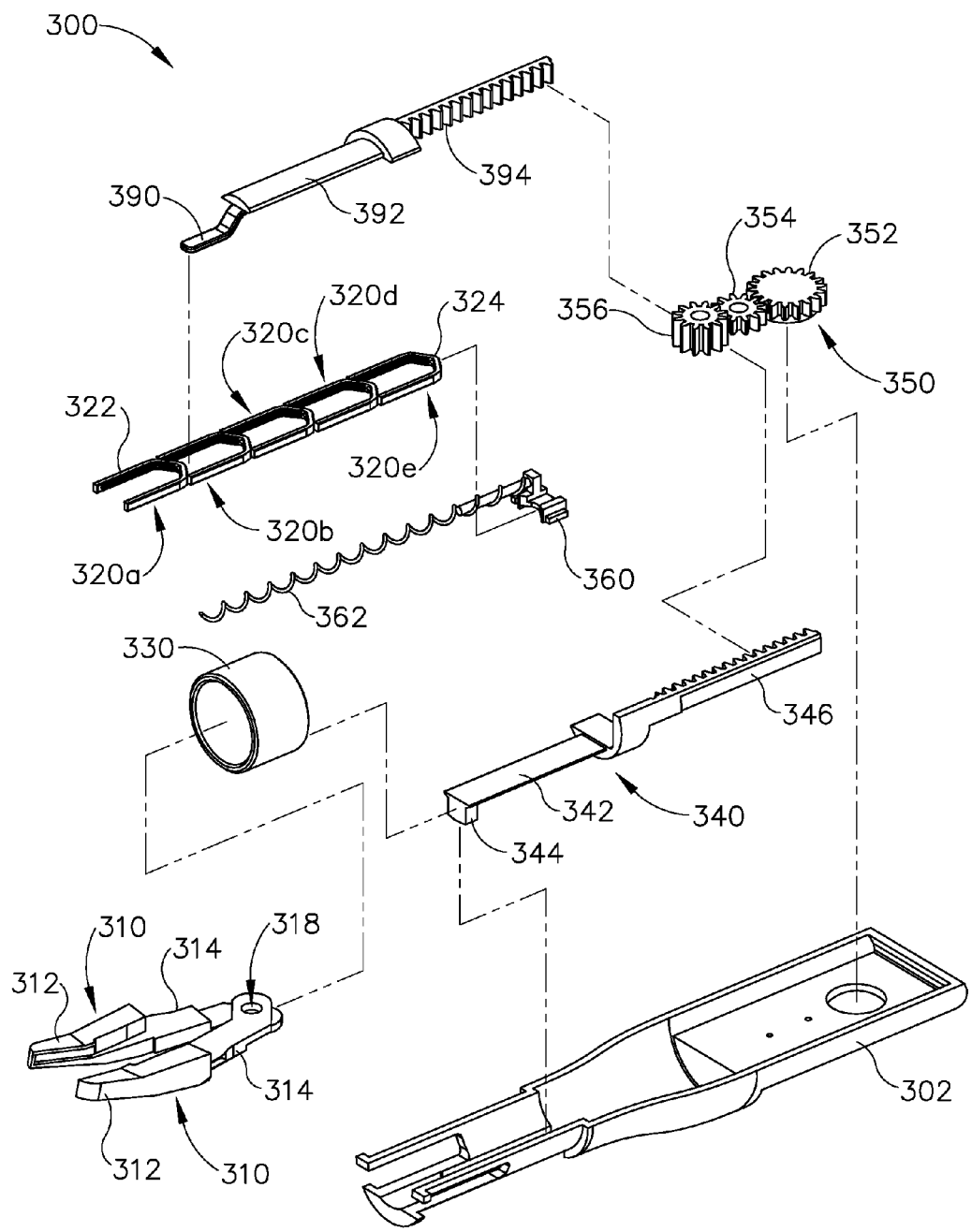
FIG. 17 depicts an exploded perspective view of the cartridge of FIG. 15, with a housing of the cartridge shown in cross-section.

Cartridge (300) of the present example is operable to deform clip (320) by actuating a pair of jaws (310), which extend distally from housing (302). As best seen in FIG. 17, each jaw (310) has a distal end (312) and laterally presented bearing surface (314). Jaws (310) overlap with each other and are pivotably secured together by a pin (not shown), which is disposed in overlapping openings (318) at the proximal ends of jaws (310). Jaws (310) are actuated by an actuation collar (330), which is driven by a driver (340). Collar (330) is slidably disposed about the exterior of housing (302) and is operable to move between a distal position and a proximal position as will be described in greater detail below. As best seen in FIG. 17, driver (340) comprises a distally projecting arm (342) having a coupling feature (344) that couples driver (340) with collar (330). Driver (340) also includes a proximally projecting rack (346).

Rack (346) has teeth that mesh with teeth of a pinion gear (356), which is rotatably supported in housing (302). The teeth of pinion gear (356) mesh with the teeth of an idler gear (354), which is also rotatably supported in housing (302). The teeth of idler gear (354) mesh with the teeth of a drive gear (352), which is also rotatably supported in housing (302). Drive gear (352) is an integral feature of rotary input (350). It should therefore be understood that when key (48) rotates rotary input (350), such rotation will ultimately be communicated to pinion gear (356) via gears (352, 354). It should also be understood that rotation of pinion gear (356) will cause longitudinal translation of rack (346), which will in turn cause longitudinal translation of collar (330). As will be described in greater detail below, this longitudinal translation of collar (330) will transition jaws (310) between an open state and a closed state.

In the present example, pinion gear (356) is taller than gears (352, 354). Rack (346) engages pinion gear (356) at an upper section of pinion gear (356) while idler gear (354) engages pinion gear (356) at a lower section of pinion gear (356). Drive gear (352) is located at the same vertical position as idler gear (354) such that the vertical position of drive gear (352) corresponds with the lower section of pinion gear (356). This vertical arrangement of gears (352, 354, 356) enables rack (346) to pass above gears (352, 354), without engaging gears (352, 354), as rack (346) translates to a proximal position. Of course, gears (352, 354, 356) may instead be positioned in any other suitable arrangement that enables rack (346) to translate longitudinally without engaging gears (352, 354).

In the present example, cartridge (300) houses five surgical clips (320a, 320b, 320c, 320d, 330e). Alternatively, cartridge (300) may house any other suitable number of clips (320). As best seen in FIG. 17, cartridge (300) includes a biasing saddle (360) coupled with a resilient member (362). Resilient member (362) is further engaged with housing (302) and is configured to resiliently urge biasing saddle (360) distally. Biasing saddle (360) is configured to engage the proximal-most clip (320e) and thereby urge the proximal-most clip (320e) distally. Clips (320a, 320b, 320c, 320d, 320d) are arranged to contact each other in a line such that the distal bias provided to clip (320e) is further provided to the rest of clips (320a, 320b, 320c, 320d).

Cartridge (300) further includes a retainer (390) that is configured to selectively retain clips (320) in housing (302). Retainer (390) comprises a dogleg-shaped leaf spring. A proximal end of retainer (390) is fixedly secured to an arm (392). A rack (394) projects proximally from arm (392). The teeth of rack (394) are engaged with the teeth of pinion gear (356) on the lateral side of pinion gear (356) that is opposite to the lateral side of pinion gear (356) where rack (346) is engaged with pinion gear (356). It should therefore be understood that rotation of pinion gear (356) in a first angular direction will cause simultaneous distal movement of rack (346) and proximal movement of rack (394); while rotation of pinion gear (356) in a second angular direction will cause simultaneous proximal movement of rack (346) and distal movement of rack (394).

In the present example, and as will be described in greater detail below, retainer (390) provides powered indexing of clips (320) relative to jaws (310) as jaws (310) are actuated successively. Retainer (390) also prevents the distal-most clip (320a) from traveling proximally while jaws (310) are in the open position. It should also be understood that jaws (310) may include features that prevent the resilient bias of biasing saddle (360) and resilient member (362) from prematurely ejecting the distal-most clip (320a) from jaws (310). Various suitable ways in which clips (320) may be selectively retained in cartridge (300) will be apparent to those of ordinary skill in the art in view of the teachings herein.

Figure 18A:
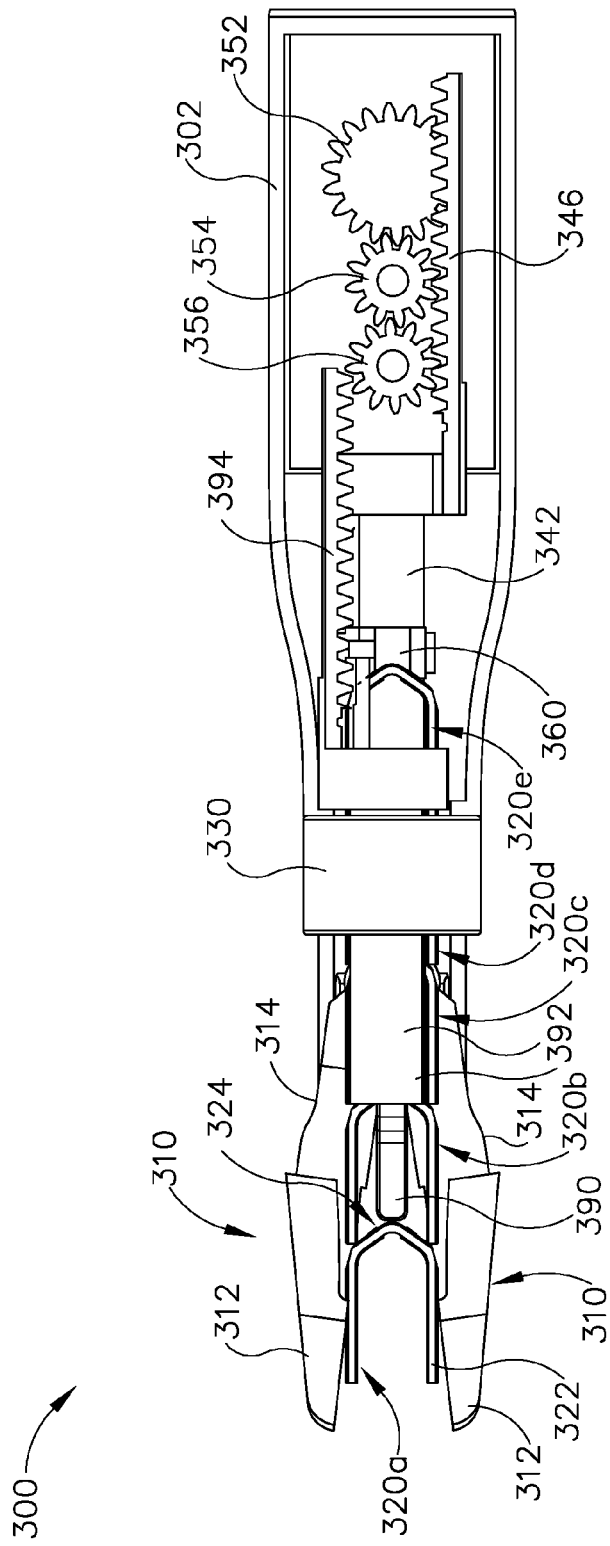
FIG. 18A depicts a top cross-sectional view of the cartridge of FIG. 15, with a first clip positioned for clamping by jaws of the cartridge.

FIGS. 18A-18C show cartridge (300) at various stages of operation. In particular, FIG. 18A shows cartridge (300) in a pre-actuated state where distal-most clip (320a) is positioned between open jaws (310). In this state, actuation collar (330) is spaced proximally of bearing surfaces (314), which protrude outwardly from housing (302). Cartridge (300) may be loaded in cartridge receiving assembly (50) while cartridge (300) is in the pre-actuated state shown in FIG. 18A.

After the operator loads cartridge (300) in cartridge receiving assembly (50), the operator may position cartridge (300) in a location where a vessel or other anatomical structure is positioned between legs (322) of distal-most clip (320a). The operator may then actuate first input (12) to drive rotation of key (48) as described above. This rotation of key (48) in a first angular direction is communicated to rotary input (350), thereby rotating drive gear (352) in the first angular direction as shown in FIG. 18B. This rotation of drive gear (352) is communicated to pinion gear (356) via idler gear (354). The rotation of pinion gear (356) drives rack (346) distally while simultaneously driving rack (394) proximally. The distal movement of rack (346) drives collar (330) distally via arm (342) and coupling feature (244). As collar (230) moves distally, collar (230) bears on bearing surfaces (214) of jaws (210) and thereby drives distal ends (212) of jaws (210) toward each other.

As distal ends (312) of jaws (310) pivot toward each other, distal ends (312) urge legs (322) of distal-most clip (320a) toward each other, thereby compressing distal-most clip (320a). As shown in FIG. 18B, legs (322) are compressed against each other in apposition. While not shown in FIG. 18B, it should be understood that a vessel or other anatomical structure may be captured between legs (322) such that legs (322) provide ligation of the vessel or other anatomical structure. The malleable properties of the material forming clip (320) will maintain the compressed configuration until clip (320) is absorbed or otherwise disintegrates.

The proximal movement of rack (394) as seen in the transition from FIG. 18A to FIG. 18B translates retainer (390) proximally via arm (392). In particular, retainer (390) transitions from engaging crown (324) of distal-most clip (320a) to engaging crown (324) of second clip (320b). During this transition, retainer (390) may flex slightly to slide over a top surface of second clip (320b) before snapping back downwardly to position the distal tip of retainer (390) just proximal to the proximal facing surface of crown (324) of second clip (320b).

When the operator releases first input (12), key (48) will rotate in a second angular direction. This rotation of key (48) in a second angular direction is communicated to rotary input (350), thereby rotating drive gear (352) in the second angular direction as shown in FIG. 18C. This rotation of drive gear (352) is communicated to pinion gear (356) via idler gear (354). The rotation of pinion gear (356) drives rack (346) proximally. The proximal movement of rack (346) drives collar (330) proximally via arm (342) and coupling feature (344). As collar (330) moves proximally, collar (330) disengages bearing surfaces (314) of jaws (310), allowing distal ends (312) of jaws (310) to pivot outwardly away from each other.

As distal ends (312) of jaws (310) pivot away from each other, jaws (310) release the deformed distal-most clip (320a). In some versions, a leaf spring, torsion spring, or other kind of resilient member urges jaws (310) toward the open position as soon as collar (330) is translated proximally. In some other versions, a camming feature drives jaws (310) toward the open position as collar (330) is translated proximally. Various suitable components, features, and configurations that may be used to urge jaws (310) toward the open position as collar (330) is translated proximally will be apparent to those of ordinary skill in the art in view of the teachings herein.

In addition to releasing the deformed distal-most clip (320a), and as shown in FIG. 18C, the opened jaws (310) will receive second clip (320b), which was previously just proximal to distal-most clip (320b). In particular, rotation of gears (352, 354, 356) in the transition from the state shown in FIG. 18B to the state shown in FIG. 18C will drive rack (394) distally, which will in turn drive retainer (390) distally. As noted above, the distal end of retainer (390) is engaged with the proximal face of crown (324) of second clip (320b) in the state shown in FIG. 18B. Thus, as retainer (390) advances distally from the position shown in FIG. 18B to the position shown in FIG. 18C, retainer (390) drives second clip (320b) distally to position clip (320b) between open jaws (310). Biasing saddle (360) and resilient member (362) will urge the rest of the clips (320c, 320d, 320e) distally, maintaining the adjacent positioning of clips (320c, 320d, 320e) proximal to second clip (320b).

It should be understood from the foregoing that an operator may successively apply each clip (320) in cartridge (300) by repeatedly actuating and releasing first input (12). In the event that all of the clips (320) in cartridge (300) have been used and the operator wishes to apply additional clips (320), the operator may simply remove the spent cartridge (300) from cartridge receiving assembly (50) and secure a new cartridge (300) to cartridge receiving assembly (50). Alternatively, the operator may secure any other cartridge described herein to cartridge receiving assembly (50), such as to perform additional surgical tasks of different modalities.

D. Exemplary Suture Anchor Clip Applier Cartridge

Figure 19:
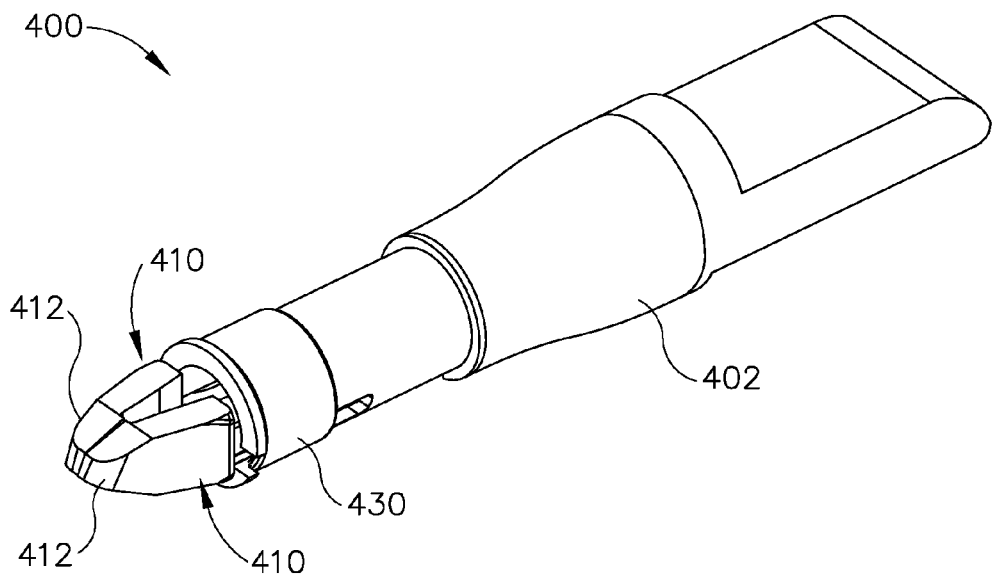
FIG. 19 depicts a perspective view of another exemplary alternative cartridge that may be used with the instrument of FIG. 1.
Figure 20:
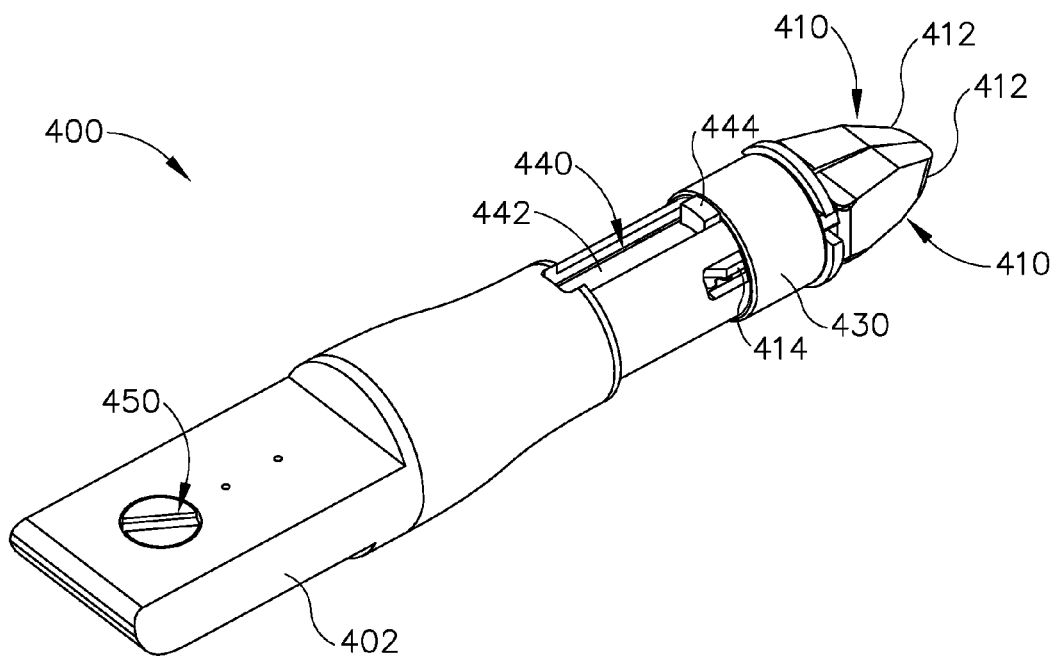
FIG. 20 depicts another perspective view of the cartridge of FIG. 19.

FIGS. 19-20 show another exemplary cartridge (400) that may be readily used with instrument (10). In particular, cartridge (400) is configured to be removably received in cartridge receiving assembly (50). It should be understood that cartridge (400) may be selectively secured in and released from cartridge receiving assembly (50) in the same manner in which cartridge (30) is selectively secured in and released from cartridge receiving assembly (50) as described above. Cartridge (400) includes a housing (402) and a rotary input (450). As best seen in FIG. 20, rotary input (450) includes a slot that is configured to mate with key (48) of cartridge receiving assembly (50), such that cartridge (400) is actuated by rotation of key (48) as will be described in greater detail below. It should therefore be understood that cartridge (400) is actuated by actuation of first input (12). As will also be described in greater detail below, cartridge (400) will apply a suture anchor clip (420) when cartridge (400) is actuated by first input (12).

Figure 21:
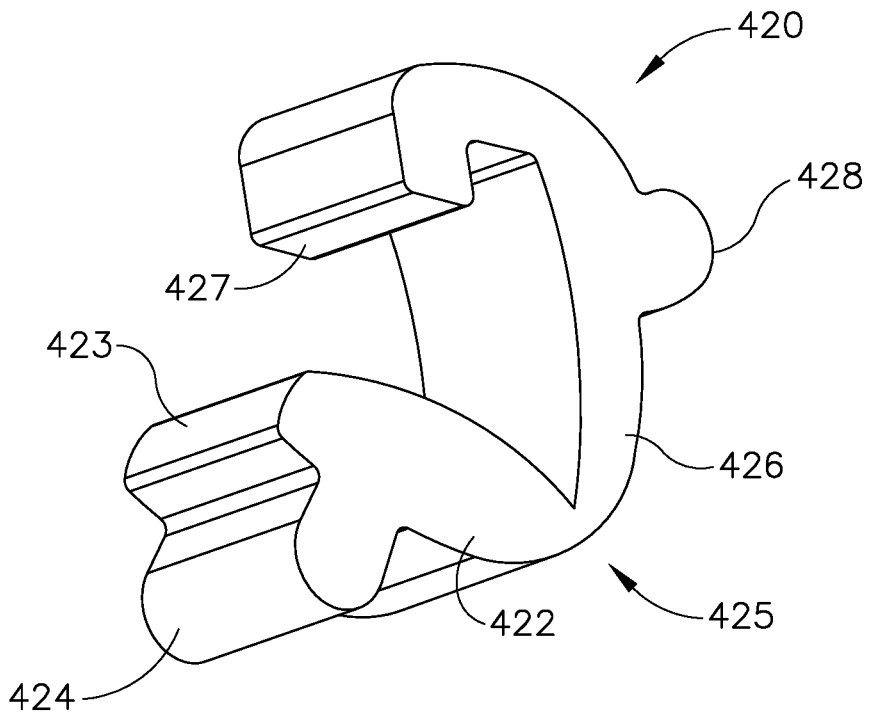
FIG. 21 depicts a perspective view of a suture anchor clip of the cartridge of FIG. 19, in a non-actuated state.
Figure 22:
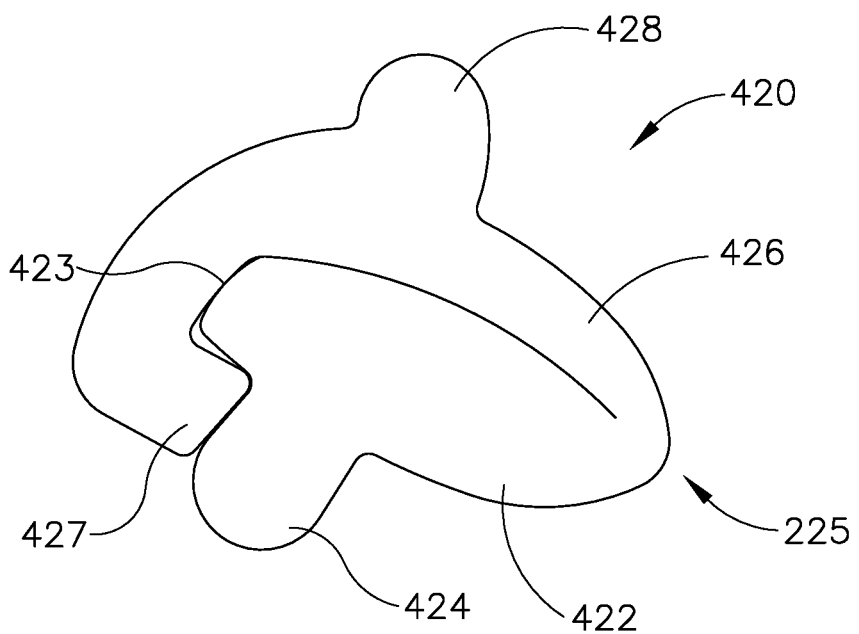
FIG. 22 depicts a side elevational view of the suture anchor clip of FIG. 21, in an actuated state.
Figure 23:
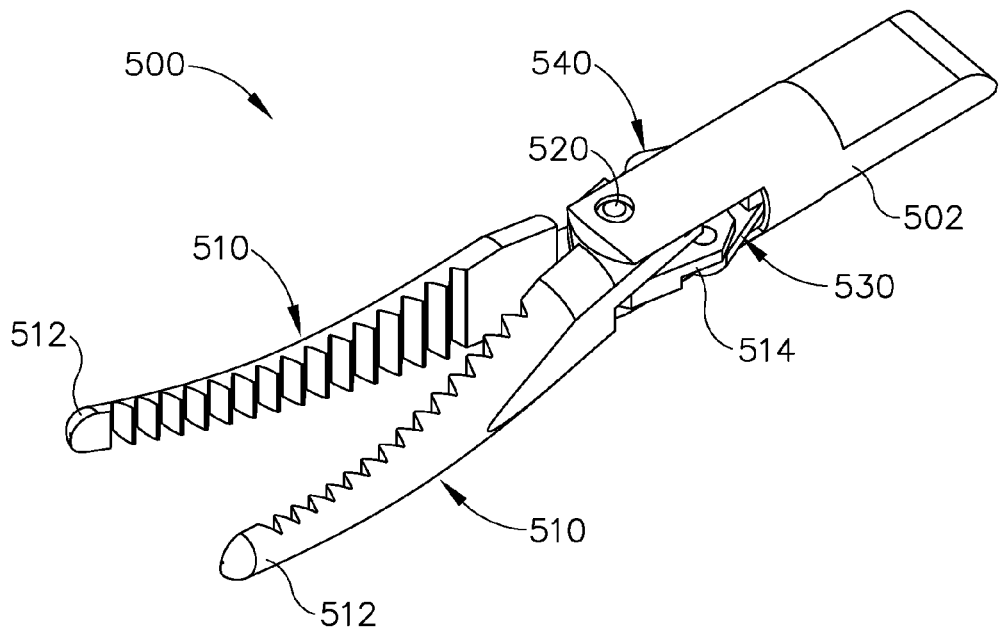
FIG. 23 depicts a perspective view of another exemplary alternative cartridge that may be used with the instrument of FIG. 1.

Cartridge (400) is configured to provide instrument (10) with functionality similar to that of a LAPRA-TY® Suture Clip Applier instrument by Ethicon Endo-Surgery, Inc. of Cincinnati, Ohio. In particular, cartridge (400) is operable to apply a selected number of suture anchor clips (420) to secure the position of suture that is applied to tissue. As best seen in FIGS. 21-22, each clip (420) of the present example has a pair of legs (422, 426) that are joined together by a living hinge (425). First leg (422) has a latching feature (423) and an engagement feature (424). Second leg (426) has a latching feature (427) and an engagement feature (428). Latching features (423, 427) are configured to engage each other to bind clip (420) in a latched configuration as shown in FIG. 22. In this latched configuration, clip (420) is configured to securely hold a length of suture between legs (422, 426). Clip (420) is also sized such that clip (420) will not pull through tissue when placed under a normal load. Thus, when a length of suture is passed through tissue to form one or more stitches, a clip (420) may be secured to the suture at each end of the stitch or stitches in order to secure the stitch or stitches. Engagement features (424, 428) may assist in preventing clip (420) from being pulled through the tissue. In addition or in the alternative, engagement features (424, 428) may assist in holding and/or manipulation of clip (420) by jaws (410) of cartridge (400). In some other versions, clips (420) are configured in accordance with at least some of the teachings of U.S. Pub. No. 2012/0290005, entitled "Suture Fastening Device," published Nov. 15, 2012, now U.S. Pat. No. 9,247,938, issued on Feb. 2, 2016, the disclosure of which is incorporated by reference herein. Other suitable forms that clips (420) may take will be apparent to those of ordinary skill in the art in view of the teachings herein.

Aside from applying clips (420) instead of clips (320), and having jaws (410) that are configured differently to accommodate clips (420), cartridge (400) of this example is substantially identical to cartridge (300). Thus, rotation of rotary input (450) will cause translation of a drive collar (430) relative to housing (402) via a driver (440). Driver (440) includes an arm (442), a coupling feature (444), and a rack (not shown) just like driver (340) described above. Collar (430) will bear against bearing surfaces (414) of jaws (410) as collar (430) is translated distally, thereby pivoting the distal ends (412) of jaws (410) toward each other to transition the distal-most clip (420) from the open configuration shown in FIG. 21 to the closed configuration shown in FIG. 22. When collar (430) is subsequently translated proximally, jaws (410) will transition back to the open configuration, thereby releasing the applied clip (420) and allowing the next clip to be indexed between jaws (410). The internal components of cartridge (400) may be configured and operable just like the internal components of cartridge (300) as described above.

It should be understood from the foregoing that an operator may successively apply each clip (420) in cartridge (400) by repeatedly actuating and releasing first input (12). In the event that all of the clips (420) in cartridge (400) have been used and the operator wishes to apply additional clips (420), the operator may simply remove the spent cartridge (400) from cartridge receiving assembly (50) and secure a new cartridge (300) to cartridge receiving assembly (50). Alternatively, the operator may secure any other cartridge described herein to cartridge receiving assembly (50), such as to perform additional surgical tasks of different modalities.

E. Exemplary Cartridge with Grasping Jaws

Figure 24:
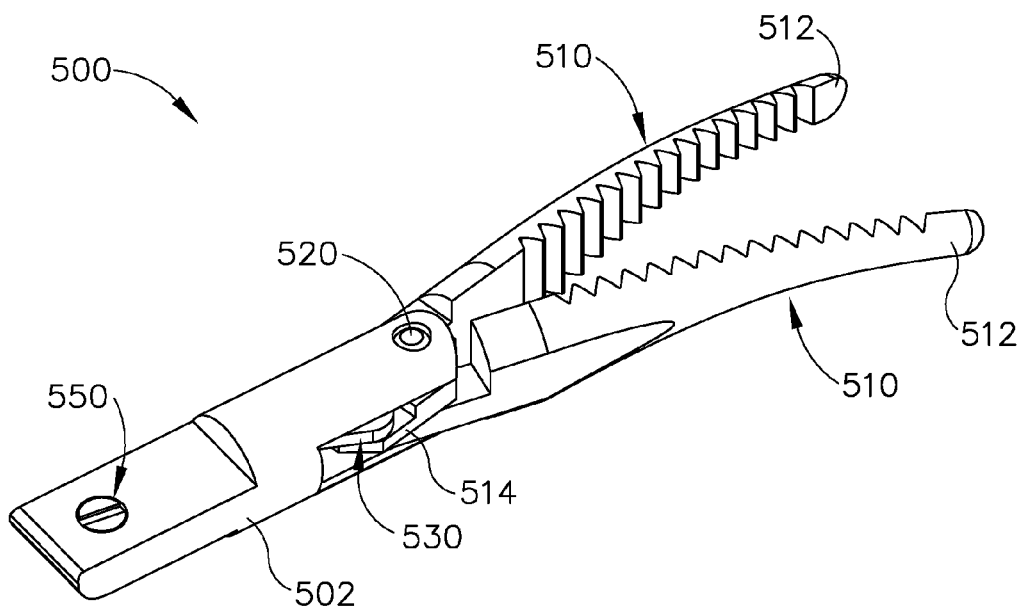
FIG. 24 depicts another perspective view of the cartridge of FIG. 23.

FIGS. 23-26C show another exemplary cartridge (500) that may be readily used with instrument (10). In particular, cartridge (500) is configured to be removably received in cartridge receiving assembly (50). Cartridge (500) includes a housing (502) and a rotary input (550). It should be understood that cartridge (500) may be selectively secured in and released from cartridge receiving assembly (50) in the same manner in which cartridge (30) is selectively secured in and released from cartridge receiving assembly (50) as described above. As best seen in FIG. 24, rotary input (550) includes a slot that is configured to mate with key (48) of cartridge receiving assembly (50), such that cartridge (500) is actuated by rotation of key (48) as will be described in greater detail below. It should therefore be understood that cartridge (500) is actuated by actuation of first input (12). As will also be described in greater detail below, cartridge (500) will selectively grasp tissue or other objects with jaws (510) when cartridge (500) is actuated by first input (12).

Figure 25:
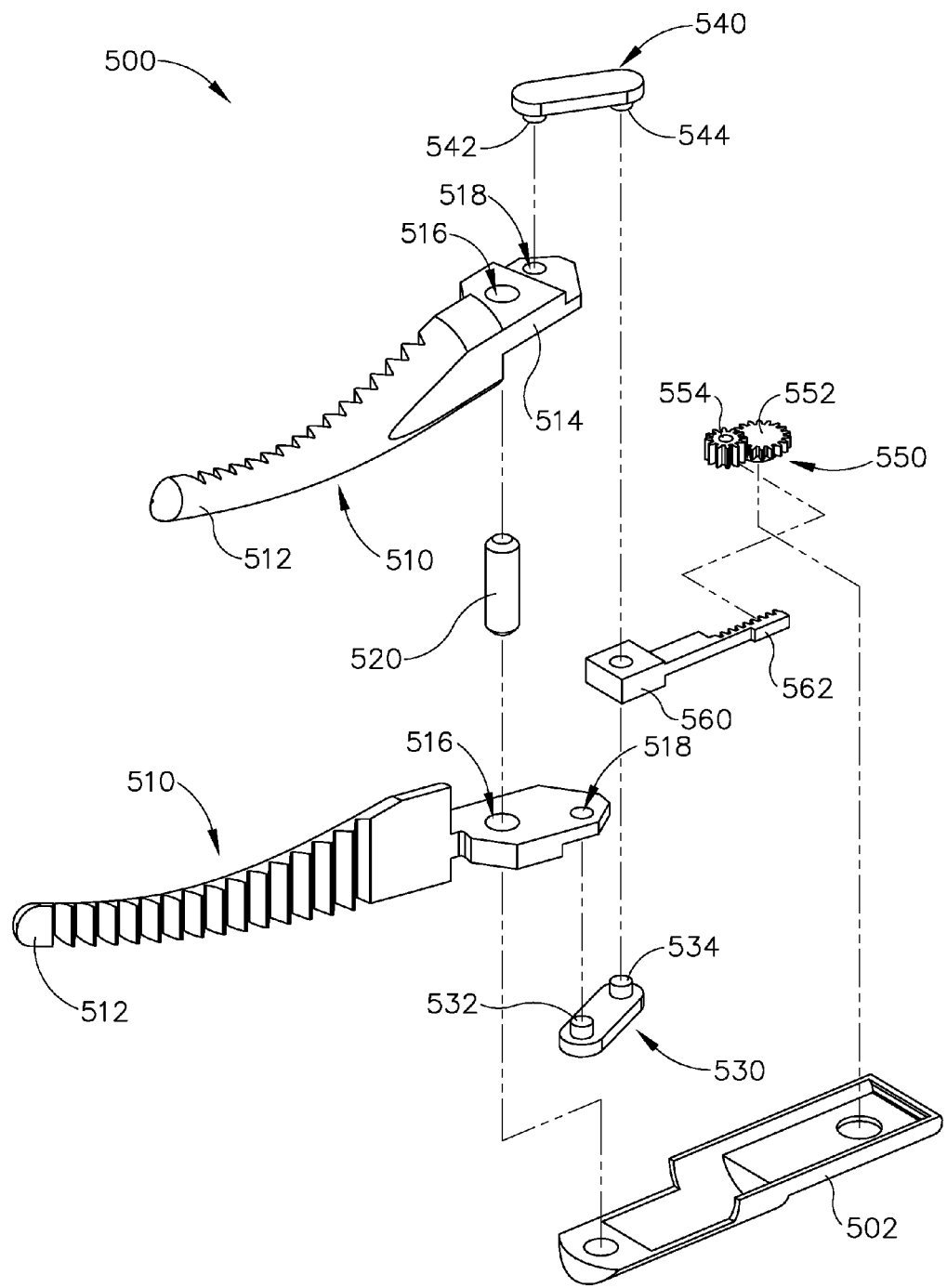
FIG. 25 depicts an exploded perspective view of the cartridge of FIG. 23, with a housing of the cartridge shown in cross-section.

Cartridge (500) is configured to provide instrument (10) with functionality similar to that of a conventional grasper instrument. In particular, cartridge (500) includes a pair of grasping jaws (510) with opposing surfaces that are operable to securely grasp tissue or other objects. As best seen in FIG. 25, each jaw (510) has a distal end (512) and a proximal end (514). Proximal end (514) of each jaw (510) includes a first opening (516) and a second opening (518), which is proximal to first opening (516). Jaws (510) are positioned in an overlapping arrangement with a pin (520) disposed in openings (516). Jaws (510) are configured to pivot about pin (520), which is secured in housing (502).

Cartridge (500) also includes a first link (530) and a second link (540). First link (530) is positioned beneath proximal ends (514) of jaws (510) while second link (540) is positioned above proximal ends (514) of jaws (510). First link (530) includes an integral, upwardly extending distal post (532) and an integral, upwardly extending proximal post (534). Distal post (532) is pivotably disposed in the second opening (518) of one of the jaws (510). Second link (540) includes an integral, downwardly extending distal post (542) and an integral, downwardly extending proximal post (544). Distal post (542) is pivotably disposed in the second opening (518) of the other one of the jaws (510).

Proximal posts (534, 544) of links (530, 540) are axially aligned with each other and are each pivotably secured to the distal end of an actuator (560). The proximal end of actuator (562) includes an integral rack (562). The teeth of rack (562) mesh with the teeth of a pinion gear (554), which is rotatably supported in housing (502). The teeth of pinion gear (554) mesh with the teeth of a drive gear (552), which is also rotatably supported in housing (502). Drive gear (552) is an integral feature of rotary input (550). It should therefore be understood that when key (48) rotates rotary input (550), such rotation will ultimately be communicated to pinion gear (554) via gear (552). It should also be understood that rotation of pinion gear (554) will cause longitudinal translation of rack (562), which will in turn cause longitudinal translation of actuator (560). As will be described in greater detail below, this longitudinal translation of actuator (560) will transition jaws (510) between an open state and a closed state.

In the present example, pinion gear (554) is taller than drive gear (552). Rack (562) engages pinion gear (554) at an upper section of pinion gear (554) while drive gear (552) engages pinion gear (554) at a lower section of pinion gear (554). This vertical arrangement of gears (552, 554) enables rack (562) to pass above drive gear (552), without engaging gear (552), as rack (562) translates to a proximal position. Of course, gears (552, 554) may instead be positioned in any other suitable arrangement that enables rack (562) to translate longitudinally without engaging gear (552).

Figure 26A:
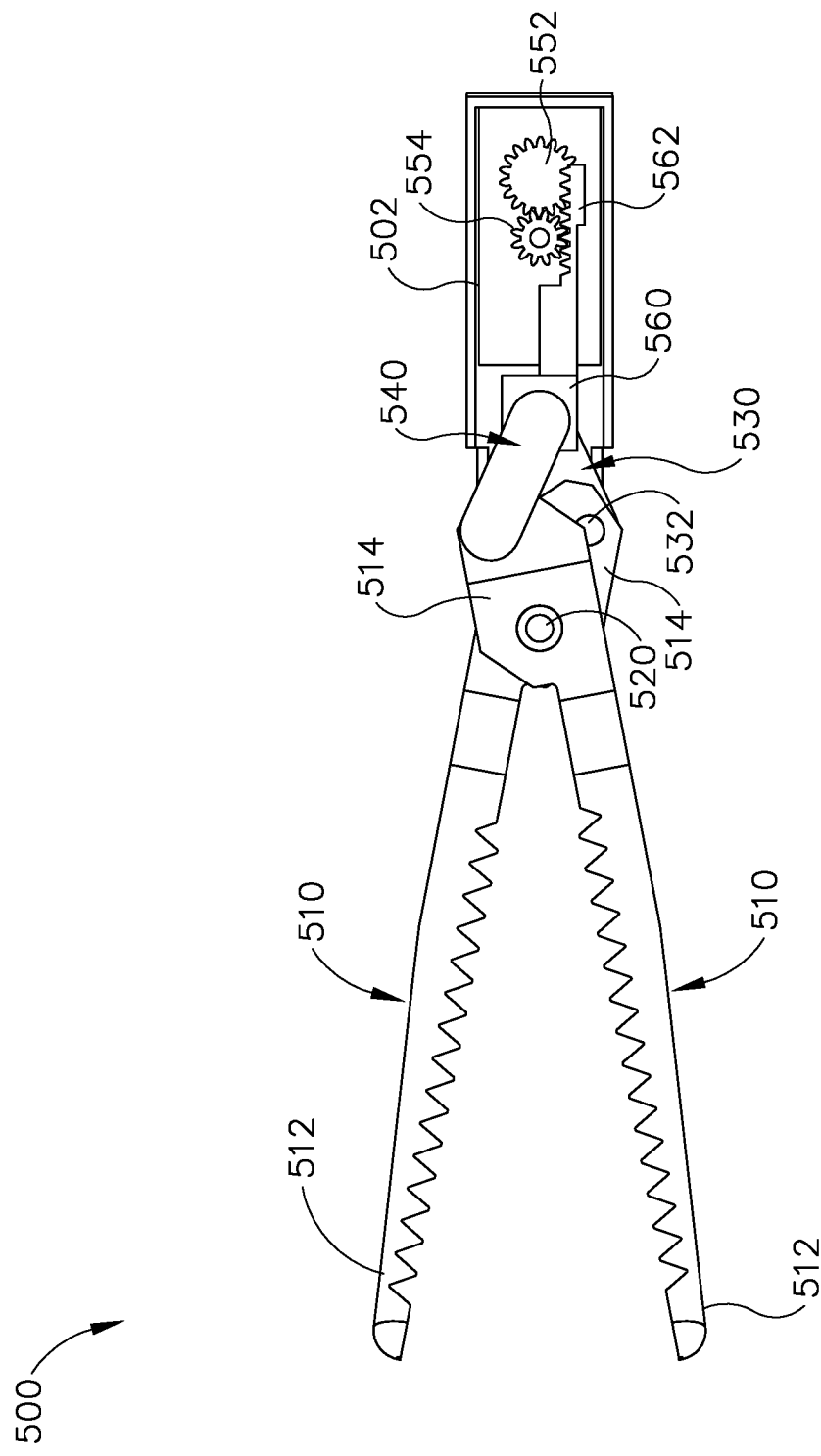
FIG. 26A depicts a top cross-sectional view of the cartridge of FIG. 23, with a jaws of the cartridge in an open state.

FIGS. 26A-26C show cartridge (500) at various stages of operation. In particular, FIG. 26A shows cartridge (500) in a pre-actuated state where jaws (510) are in an open configuration. In this state, actuator (560) is in distal position. After the operator loads cartridge (500) in cartridge receiving assembly (50), the operator may position cartridge (500) in a location where tissue or some other structure is positioned between jaws (510). The operator may then actuate first input (12) to drive rotation of key (48) as described above. This rotation of key (48) in a first angular direction is communicated to rotary input (550), thereby rotating drive gear (552) in the first angular direction as shown in FIG. 26B. This rotation of drive gear (552) is communicated to pinion gear (554), which drives actuator (560) proximally via rack (554). As actuator (560) moves proximally, the proximal ends of links (530, 540) move proximally, causing links (530, 540) to pivot about the axis shared by proximal posts (534, 544). This pivotal movement of links (530, 540) drives proximal ends (514) of jaws (510) to pivot toward each other about pin (520), thereby causing distal ends (512)

of jaws (510) to pivot toward each other about pin (520). Jaws (510) are thus transitioned to the closed configuration. Jaws (510) may be held in this closed configuration as long as desired in order to grasp tissue or some other structure.

When the operator wishes to release the tissue or other structure from the grasp of jaws (510), the operator may releases first input (12), thereby causing key (48) to rotate in a second angular direction. This rotation of key (48) in a second angular direction is communicated to rotary input (550), thereby rotating drive gear (552) in the second angular direction as shown in FIG. 26C. This rotation of drive gear (552) is communicated to pinion gear (554), which drives actuator (560) distally via rack (562). The distal movement of actuator (560) driving the proximal ends of links (530, 540) distally, causing links (530, 540) to pivot about the axis shared by proximal posts (534, 544). This pivotal movement of links (530, 540) drives proximal ends (514) of jaws (510) to pivot away from each other about pin (520), thereby causing distal ends (512) of jaws (510) to pivot away each other about pin (520). Jaws (510) are thus transitioned back to the open configuration. As jaws (510) pivot back to the open configuration, jaws (510) release the tissue or other structure that had been grasped between jaws (510).

It should be understood from the foregoing that an operator may selectively grasp and release tissue or other structures any desired number of times by repeatedly actuating and releasing first input (12). In the event that the operator wishes to perform some other task using a different modality, the operator may simply remove cartridge (500) from cartridge receiving assembly (50) and secure a different kind of cartridge (e.g., any other cartridge described herein) to cartridge receiving assembly (50).

F. Exemplary Cartridge with Scissor Blades

Figure 27:
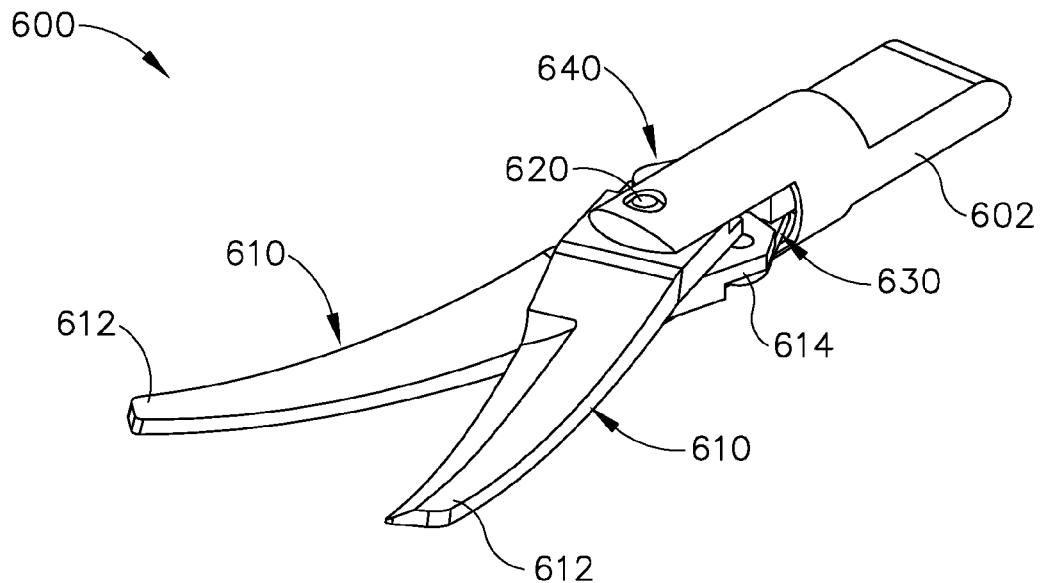
FIG. 27 depicts a perspective view of another exemplary alternative cartridge that may be used with the instrument of FIG. 1.
Figure 28:
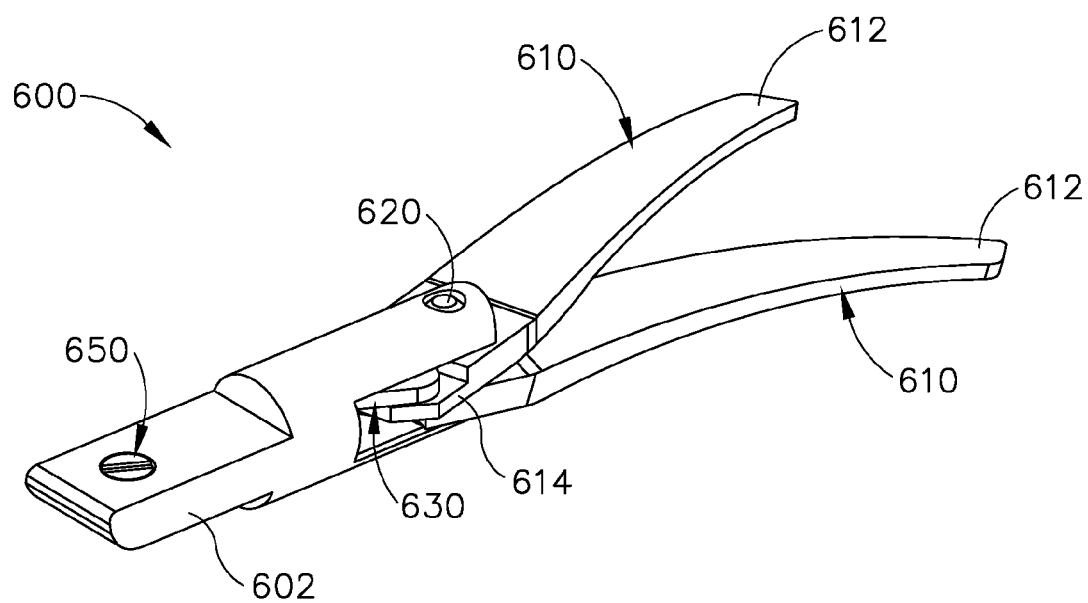
FIG. 28 depicts another perspective view of the cartridge of FIG. 27.

FIGS. 27-28 show another exemplary cartridge (600) that may be readily used with instrument (10). In particular, cartridge (600) is configured to be removably received in cartridge receiving assembly (50). It should be understood that cartridge (600) may be selectively secured in and released from cartridge receiving assembly (50) in the same manner in which cartridge (30) is selectively secured in and released from cartridge receiving assembly (50) as described above. Cartridge (600) includes a housing (602) and a rotary input (550). As best seen in FIG. 28, rotary input (650) includes a slot that is configured to mate with key (48) of cartridge receiving assembly (50), such that cartridge (600) is actuated by rotation of key (48) as will be described in greater detail below. It should therefore be understood that cartridge (600) is actuated by actuation of first input (12). As will also be described in greater detail below, cartridge (600) will selectively cut tissue or other objects with blades (610) when cartridge (600) is actuated by first input (12).

Cartridge (600) is configured to provide instrument (10) with functionality similar to that of a conventional scissor instrument. In particular, cartridge (600) includes a pair of scissor blades (610) that cooperate to cut tissue or other structures through a shearing action. Each blade (610) has a distal end (612) and a proximal end (614). Blades (610) are positioned in an overlapping arrangement. A pin (620) provides a pivotal coupling for blades (610). A link (630, 640) is pivotably secured to the proximal end (614) of a corresponding blade (610). Links (630, 640) are configured and operable just like links (530, 540) described above. Moreover, the rest of the internal components of cartridge (600) may be configured and operable just like the internal components of cartridge (500) as described above. Thus rotation of rotary input (650) in a first angular direction will cause blades (610) to pivot to a closed position; while rotation of rotary input (650) in a second angular direction will cause blades (610) to pivot to an open position. As blades (610) pivot from the open position to the closed position, blades (610) will cut tissue or other structures disposed between blades (610). This cutting will be provided through a shearing action from blades (610). Other than the differences between jaws (510) and blades (610), cartridge (600) may be configured and operable identically to cartridge (500) described above.

G. Exemplary Stapling Cartridge

Figure 29:
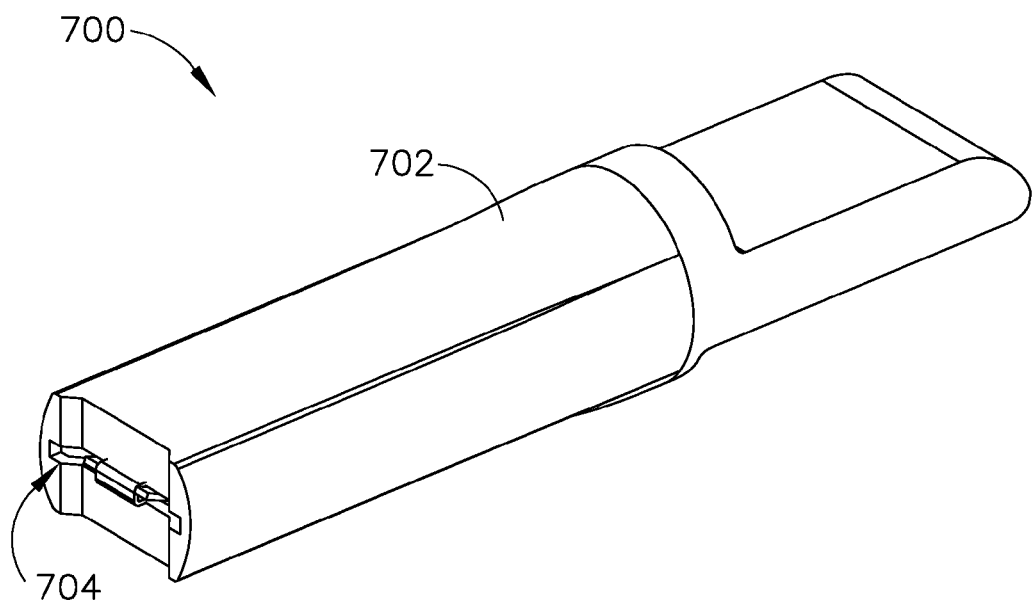
FIG. 29 depicts a perspective view of another exemplary alternative cartridge that may be used with the instrument of FIG. 1.
Figure 30:
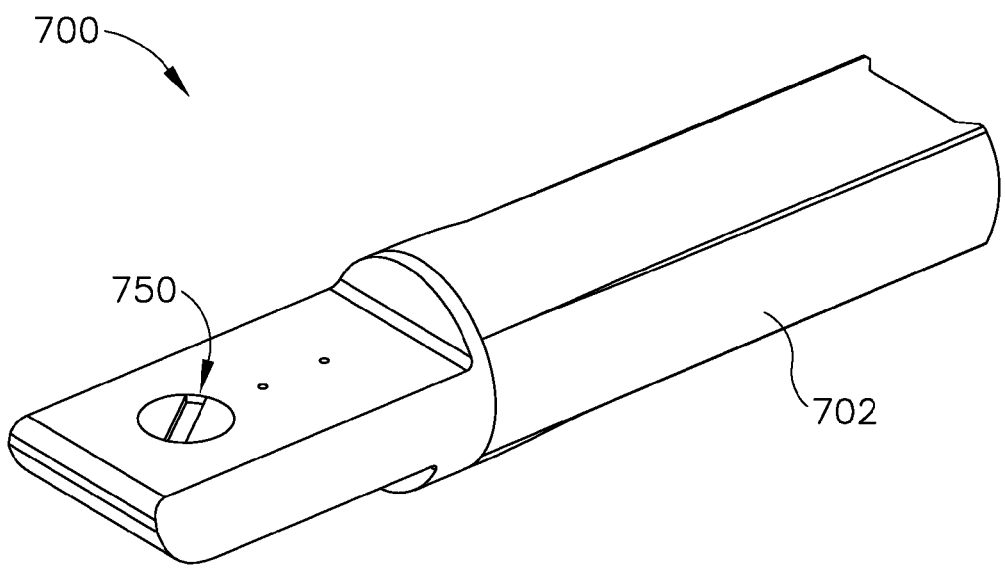
FIG. 30 depicts another perspective view of the cartridge of FIG. 29.
Figure 31:
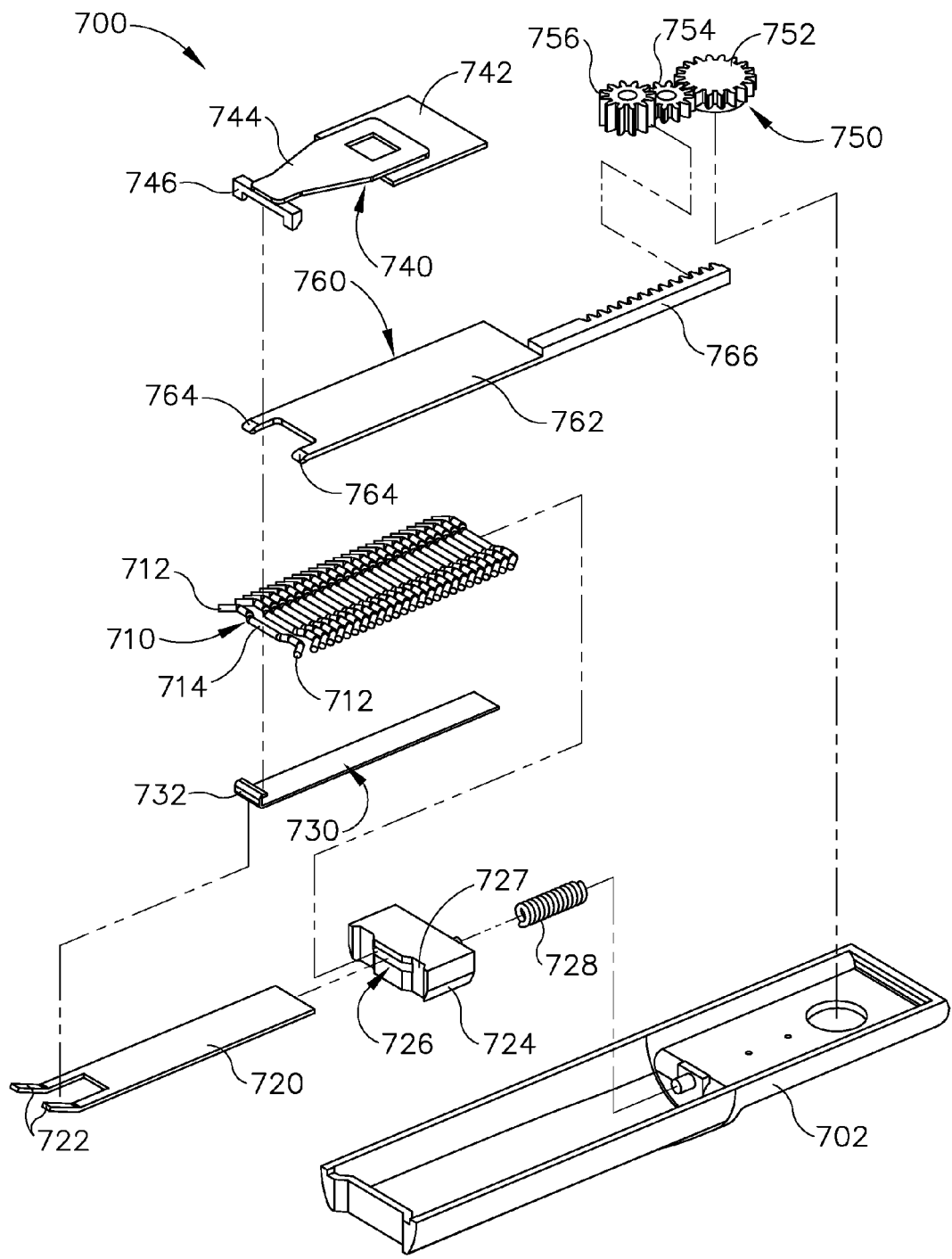
FIG. 31 depicts an exploded perspective view of the cartridge of FIG. 29, with a housing of the cartridge shown in cross-section.

FIGS. 29-31 show another exemplary cartridge (700) that may be readily used with instrument (10). In particular, cartridge (700) is configured to be removably received in cartridge receiving assembly (50). It should be understood that cartridge (700) may be selectively secured in and released from cartridge receiving assembly (50) in the same manner in which cartridge (30) is selectively secured in and released from cartridge receiving assembly (50) as described above. Cartridge (700) includes a housing (702) and a rotary input (750). As best seen in FIG. 30, rotary input (750) includes a slot that is configured to mate with key (48) of cartridge receiving assembly (50), such that cartridge (700) is actuated by rotation of key (48) as will be described in greater detail below. It should therefore be understood that cartridge (700) is actuated by actuation of first input (12). As will also be described in greater detail below, cartridge (700) will drive a formed staple (710) from an opening (704) (FIG. 29) of housing (702) when cartridge (700) is actuated by first input.

Cartridge (700) is configured to provide instrument (10) with functionality similar to that of a surgical stapling instrument. In particular, cartridge (700) is operable to apply a selected number of staples (710) in tissue. Each staple (710) of the present example comprises a pair of legs (712) and a crown portion (714). Staples (710) are provided in cartridge (700) with legs (712) in a pre-bent configuration. The configuration of the pre-bent portions of staples (710) are configured such that each staple (710) will generally form a "B" shape when staples (710) are applied to tissue as will be described in greater detail below.

As shown in FIG. 31, cartridge (700) of the present example comprises a staple guide member (720), an anvil member (730), a staple stop assembly (740), and a staple driver (760). A staple biasing saddle (724) is slidably disposed on staple guide member (720) and is configured to transfer a distally oriented resilient bias from a resilient member (728) to an array of staples (710) disposed in cartridge (700). Staple guide member (720) is configured to guide staples (710) toward anvil member (730) as staples (710) advance distally. Staple stop assembly (740) is configured to regulate distal advancement of staples (710) as cartridge (700) is repeatedly actuated. Staple driver (760) is configured to drive the distal-most staple into anvil member (730) and deform the staple against anvil (730) as will be described in greater detail below.

Figure 32:
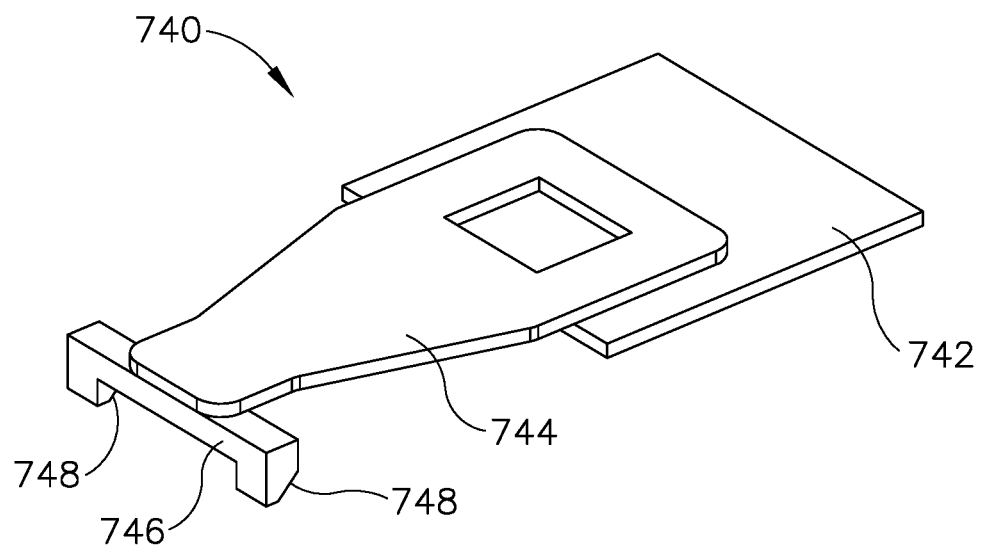
FIG. 32 depicts a perspective view of a staple stop assembly of the cartridge of FIG. 29.

As best seen in FIG. 32, staple stop assembly (740) comprises a mounting plate (742), a leaf spring (744), and a stop block (746). Mounting plate (742) is fixedly secured in housing (702). Leaf spring (744) is configured to flex to allow stop block (746) to translate along a substantially vertical plane. However, leaf spring (744) is resiliently biased to assume a flat configuration, such that leaf spring (744) will bias stop block (746) downwardly when stop block (746) travels upwardly. Stop block (748) includes a pair of chamfered proximal surfaces (748) that are configured to provide a camming action with other portions of cartridge (700) as described in greater detail below.

Figure 33:
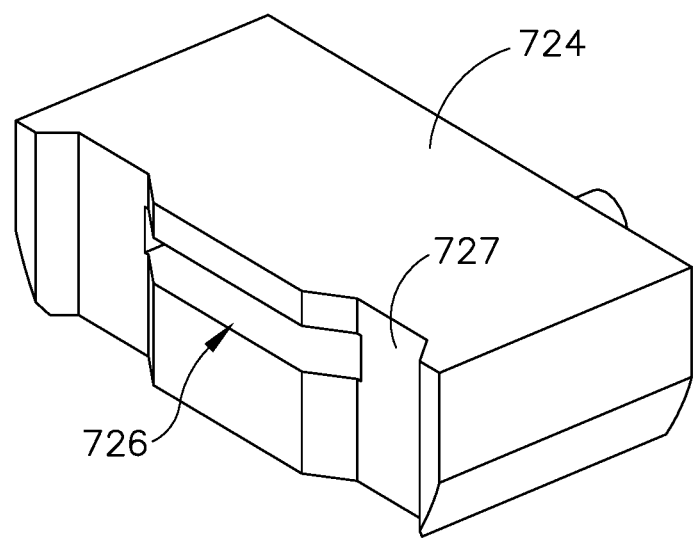
FIG. 33 depicts a perspective view of a staple biasing saddle of the cartridge of FIG. 29.

As best seen in FIG. 33, staple biasing saddle (724) comprises a slot (726) and a distal surface (727). Slot (726) is configured to slidably receive staple guide member (720) such that staple biasing saddle (724) may freely slide along staple guide member (720). Distal surface (727) has a configuration similarly to the configuration of staples (710), including the preformed bend of legs (712). Distal surface (727) is configured to bear against the proximal-most staple (710). Resilient member (728) is interposed between the proximal end of staple biasing saddle (724) and a distally facing feature of housing (702), such that resilient member (728) resiliently urges staple biasing saddle (724) distally. This distal bias is imparted to the array of staples via staple biasing saddle.

Figure 34:
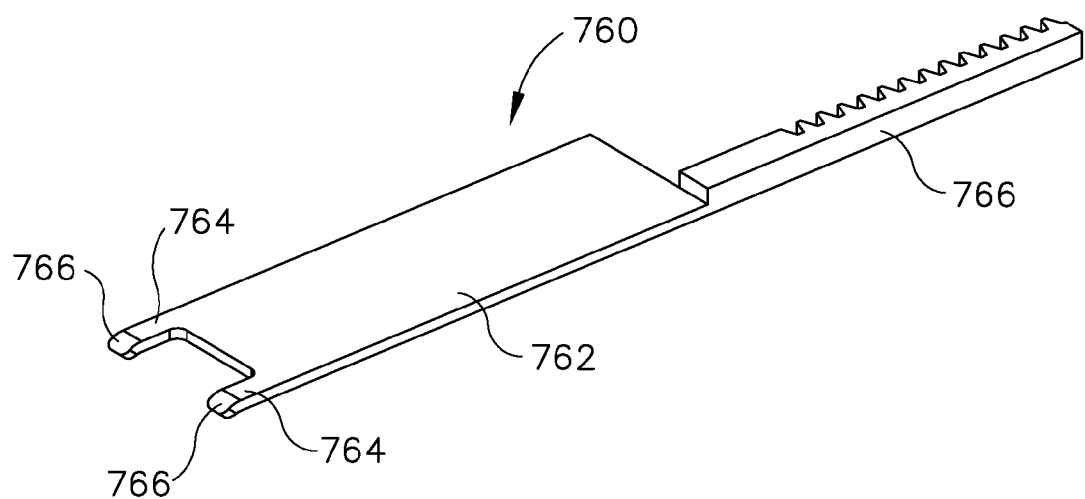
FIG. 34 depicts a perspective view of a staple driver of the cartridge of FIG. 29.

As best seen in FIG. 34, staple driver (760) comprises a plate (762) with two distally projecting prongs (764) and a proximally extending rack (766). Prongs (764) curve downwardly in the present example to provide guidance to staples (710) as will be described in greater detail below. Rack (766) includes teeth that mesh with teeth of a pinion gear (756), which is rotatably supported in housing (702). The teeth of pinion gear (756) mesh with the teeth of an idler gear (754), which is also rotatably supported in housing (702). The teeth of idler gear (754) mesh with the teeth of a drive gear (752), which is also rotatably supported in housing (702). Drive gear (752) is an integral feature of rotary input (750). It should therefore be understood that when key (48) rotates rotary input (750), such rotation will ultimately be communicated to pinion gear (756) via gears (752, 754). It should also be understood that rotation of pinion gear (756) will cause longitudinal translation of rack (766), which will in turn cause longitudinal translation of staple driver (760). As will be described in greater detail below, this longitudinal translation of staple driver (760) will cause advancement and deformation of the distal-most staple (710), thereby applying the distal-most staple (710) in tissue.

Figure 35:
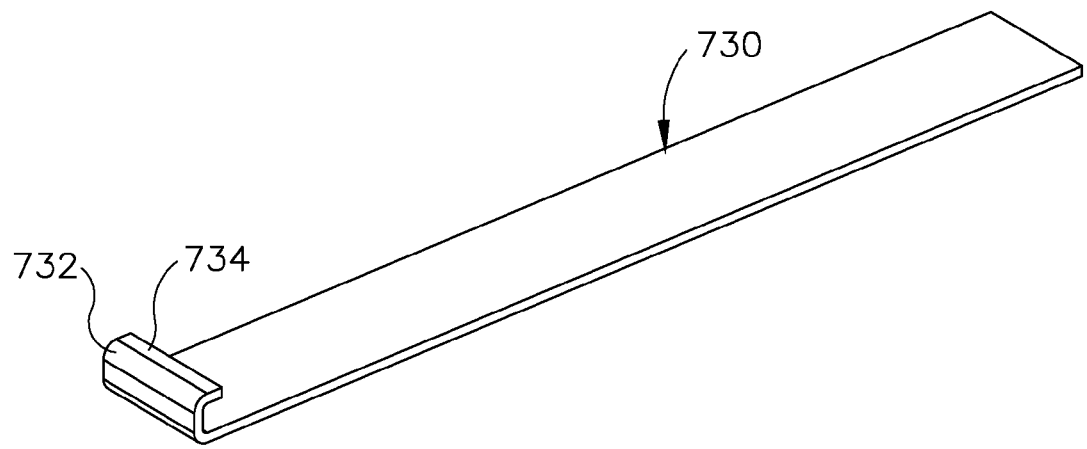
FIG. 35 depicts a perspective view of an anvil member of the cartridge of FIG. 29.

As best seen in FIG. 35, anvil member (730) comprises an upwardly projecting distal portion (732) with a proximally facing edge (734). As will be described in greater detail below, edge (734) is configured to engage the distal-most staple (710) during actuation of cartridge (700). In particular, edge (734) is configured to maintain the position and configuration of crown (714) of the distal-most staple (710) as prongs (764) of staple driver (760) deform legs (712) of the distal-most staple (710).

Figure 36:
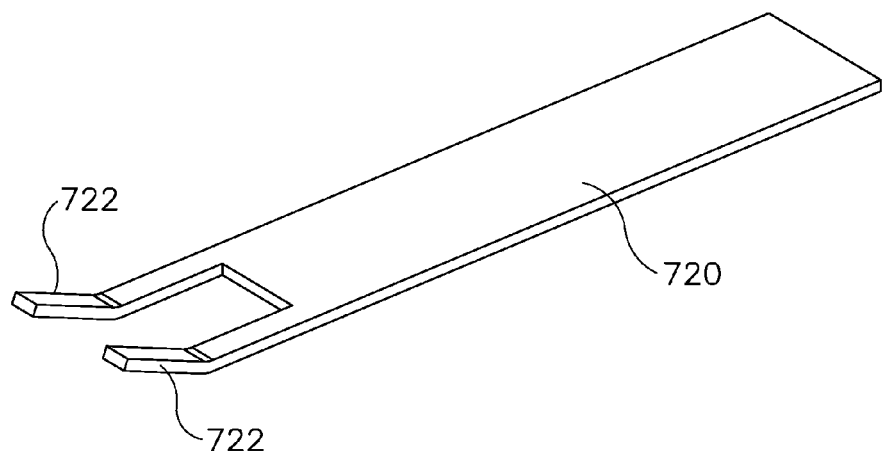
FIG. 36 depicts a perspective view of a staple guide member of the cartridge of FIG. 29.

As best seen in FIG. 36, staple guide member (720) comprises a pair of prongs (722) that extend distally and upwardly at oblique angles. Prongs (722) are configured to guide the distal-most staple (710) into engagement with proximally facing edge (734) of anvil member (730). In the present example, prongs (722) are closer together than prongs (764). Thus, as shown in FIG. 38C and as will be described in greater detail below, staple driver (760) may be advanced to a portion where prongs (764) are positioned laterally outside of prongs (722).

Figure 37A:
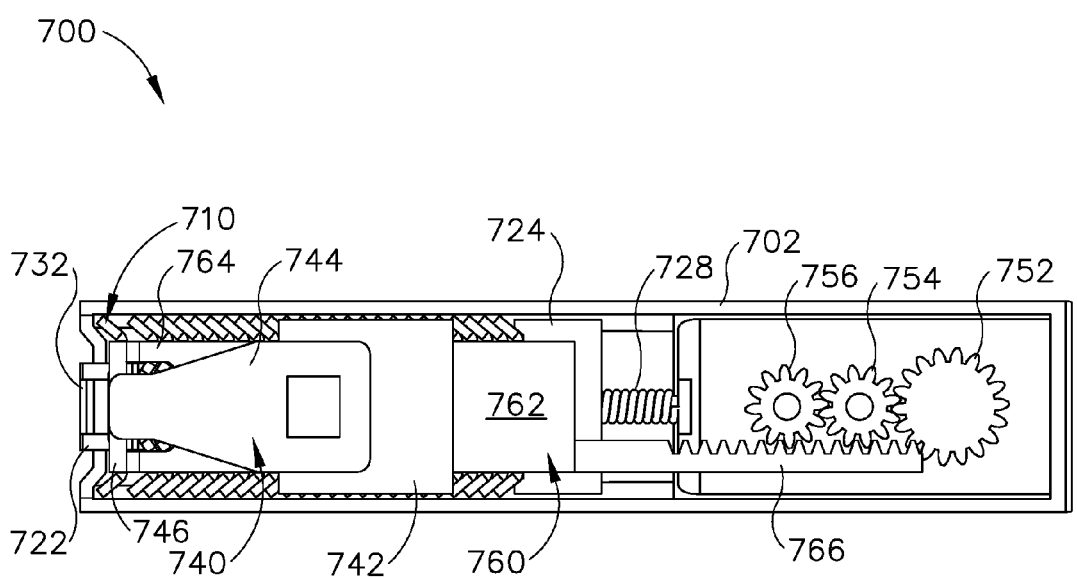
FIG. 37A depicts a top cross-sectional view of the cartridge of FIG. 29, with the cartridge in a pre-firing state.
Figure 37B:
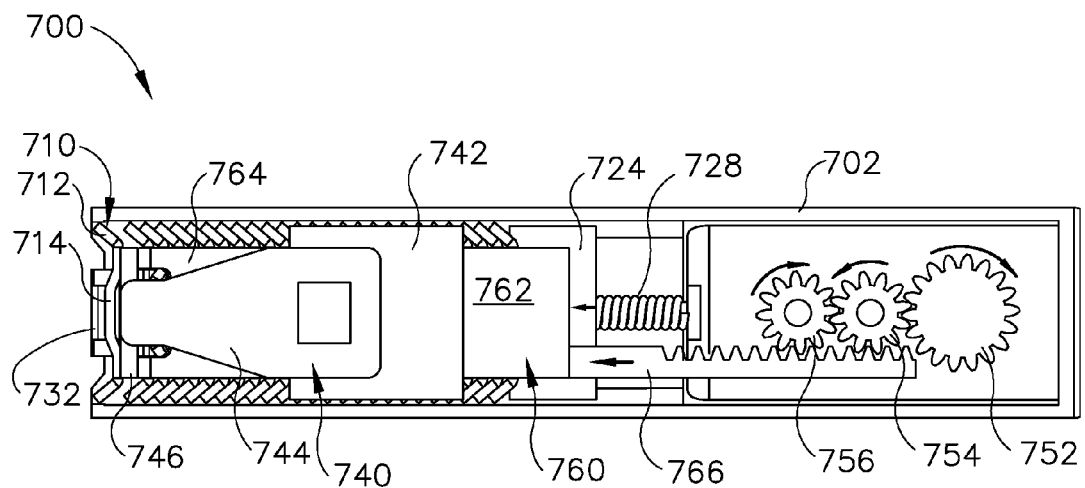
FIG. 37B depicts a top cross-sectional view of the cartridge of FIG. 29, with a first staple advanced into engagement with the anvil member.
Figure 37C:
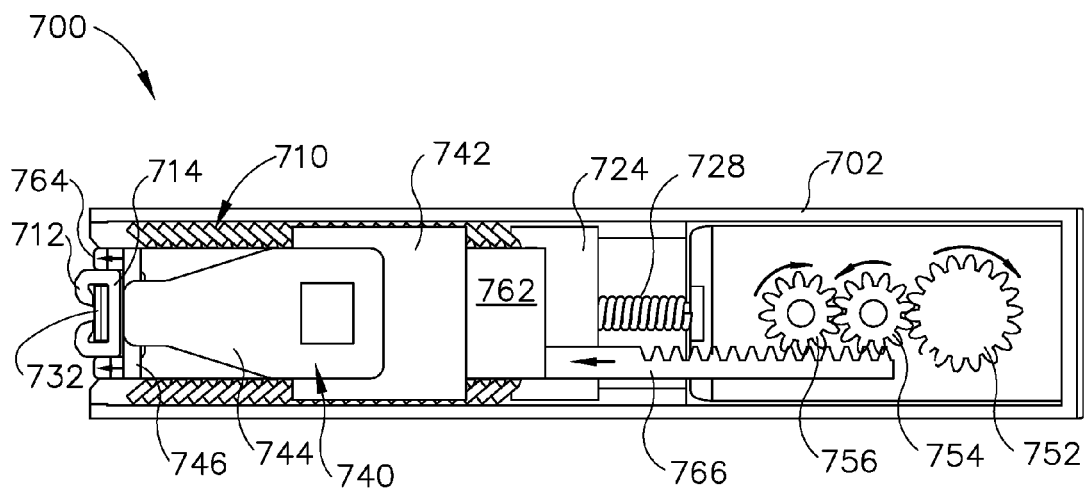
FIG. 37C depicts a top cross-sectional view of the cartridge of FIG. 29, with the staple driver deforming the first staple against the anvil member.
Figure 38A:
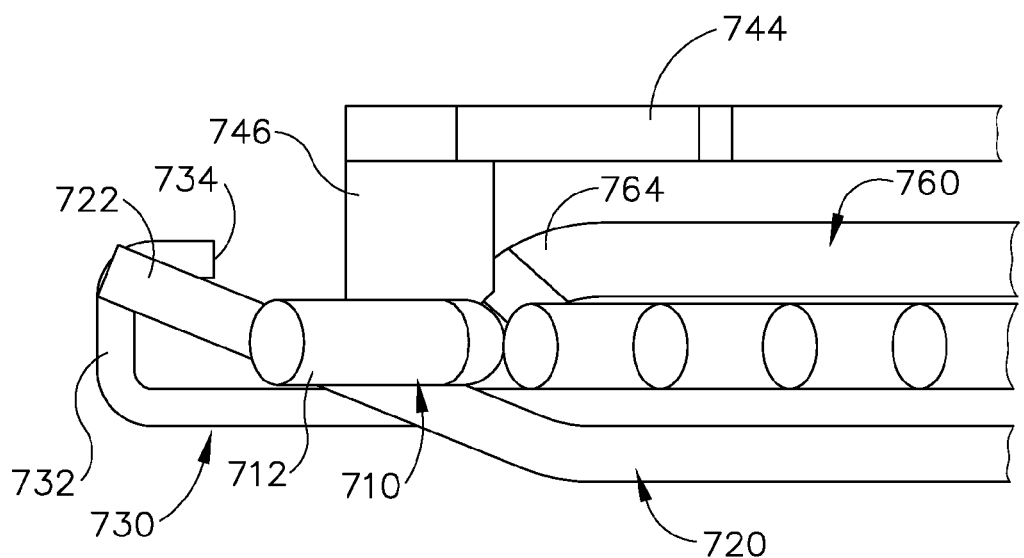
FIG. 38A depicts a partial, side elevational view of staple driving and guide components of the cartridge of FIG. 29, with the cartridge in a pre-firing state.
Figure 38B:
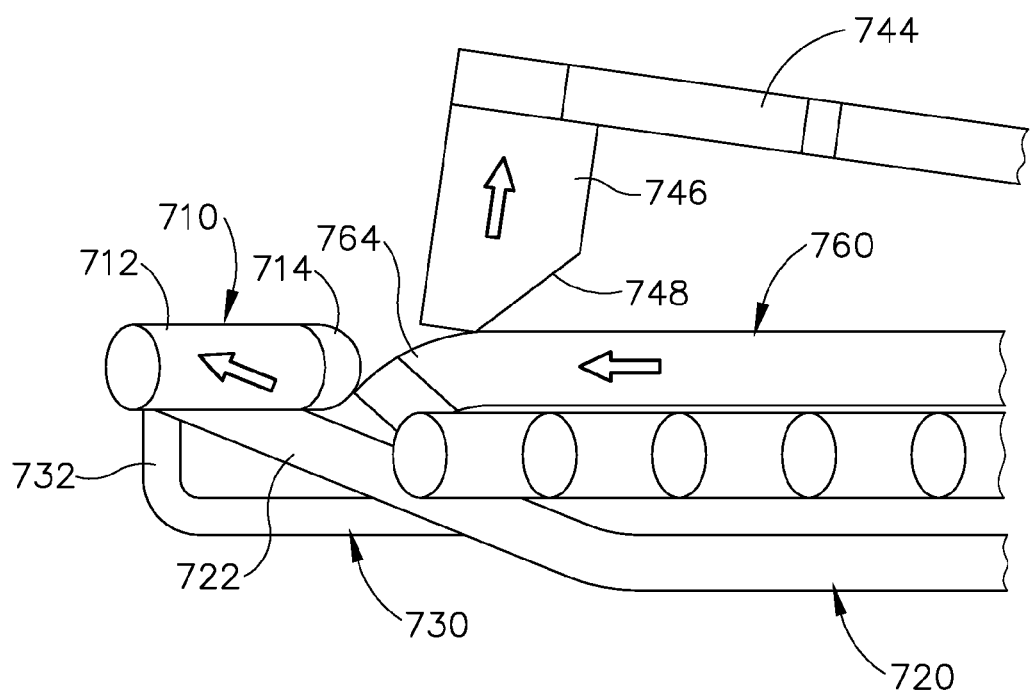
FIG. 38B depicts a partial, side elevational view of staple driving and guide components of the cartridge of FIG. 29, with the first staple advanced into engagement with the anvil member.
Figure 38C:
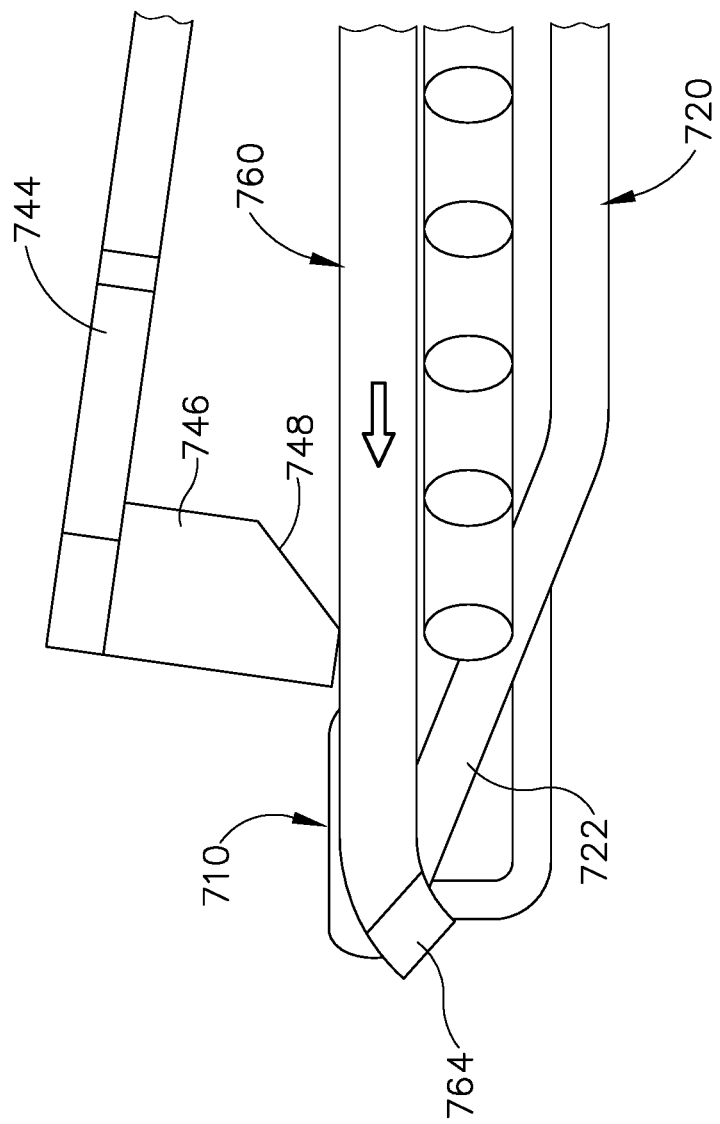
FIG. 38C depicts a partial, side elevational view of staple driving and guide components of the cartridge of FIG. 29, with the staple driver deforming the first staple against the anvil member.

FIGS. 37A-37C and 38A-38C depict cartridge (700) at various stages of actuation. In particular, FIGS. 37A and 38A depict cartridge (300) in a pre-actuated state where a distal-most staple (710) is positioned between prongs (722), stop block (746), and prongs (764). At this stage, prongs (764) separate the distal-most staple (710) from the next proximal staple (710), as driver (760) is in a proximal-most position. Cartridge (700) may be loaded in cartridge receiving assembly (50) while cartridge (700) is in the pre-actuated state shown in FIGS. 37A and 38A.

After the operator loads cartridge (700) in cartridge receiving assembly (50), the operator may position cartridge (300) in a location where the operator wishes to staple tissue (e.g., to provide tissue apposition, stomach plication, etc.). In particular, the operator would press the distal end of cartridge (700) against tissue in which the operator wishes to apply staples (710). The operator may then actuate first input (12) to drive rotation of key (48) as described above. This rotation of key (48) in a first angular direction is communicated to rotary input (750), thereby rotating drive gear (752) in a first angular direction as shown in FIG. 37B. This rotation of drive gear (752) is communicated to pinion gear (756) via idler gear (754). The rotation of pinion gear (756) drives rack (766) distally. The distal movement of rack (766) drives prongs (764) distally via plate (762). As prongs (764) advance distally, prongs drive the distal-most staple (710) distally such that crown (714) of staple (710) engages the proximally facing edge (734) of anvil member (730) as shown in FIGS. 37B and 38B. As is also shown in FIG. 38B, prongs (722) of staple guide member (720) guide staple (710) upwardly along an obliquely angled path to engage proximally facing edge (734) of anvil member (730). In addition, prongs (764) engage stop block (746) and thereby drive stop block upwardly (746), causing deformation of leaf spring (744) as staple driver (760) is driven distally.

As may also be seen in the transition from FIG. 37A to FIG. 37B, staple biasing saddle (724) translates distally under the urging of resilient member (728) during the transition from the state shown in FIGS. 37A and 38A to the state shown in FIG. 37B and FIG. 38B. The state shown in FIGS. 37B and 38B represents completion of only a portion of the distal actuation stroke of staple driver (760). As key (48) continues to drive rotary input (750) in the first angular direction, drive gear (752) continues to rotate in the first angular direction, thereby further driving gears (754, 756). The continued rotation of gear (756) drives staple driver (760) further distally via rack (766) to the position shown in FIGS. 37C and 38C. This causes prongs (764) to translate distally past the distal position of proximally facing edge (734) of anvil member (730). Since crown (714) of staple (710) remains engaged with proximally facing edge (734) of anvil member (730), the distally moving prongs (764) bend legs (712) around the lateral edges of distal portion (732) of anvil member (730). Since legs (712) already have preformed bends, the deformation provided by prongs (764) results in staple (710) generally forming a "B" shape as best seen in FIG. 37C. As legs (712) are driven to the position shown in FIG. 37C, legs (712) will penetrate the tissue that is adjacent to the distal end of cartridge (700). With legs (712) deformed to provide the "B" shape, legs (712) will secure staple (710) in the tissue. Thus, as the operator pulls cartridge (700) away from the tissue, the formed staple (710) will remain in the tissue. It should also be understood that the obliquely angled orientation of prongs (722) may assist in guiding the formed staple (710) away from cartridge (700).

When the operator releases first input (12), key (48) will rotate in a second angular direction. This rotation of key (48) in a second angular direction is communicated to rotary input (750), thereby rotating drive gear (752) in a second angular direction. This rotation of drive gear (752) is communicated to pinion gear (756) via idler gear (754). The rotation of pinion gear (756) drives needle driver (760) proximally via rack (766). The proximal movement of needle driver (760) eventually results in a state similar to that shown in FIG. 37A and FIG. 38A, with the next staple (710) being indexed for deployment by cartridge (700). It should be understood that the resilient properties of leaf spring (744) will return stop block (746) from the position shown in FIG. 38C to the position shown in FIG. 38A once staple driver (760) reaches a proximal position.

It should be understood from the foregoing that an operator may successively apply each staple (710) in cartridge (700) by repeatedly actuating and releasing first input (12). In the event that all of the staples (710) in cartridge (700) have been used and the operator wishes to apply additional staples (710), the operator may simply remove the spent cartridge (700) from cartridge receiving assembly (50) and secure a new cartridge (700) to cartridge receiving assembly (50). Alternatively, the operator may secure any other cartridge described herein to cartridge receiving assembly (50), such as to perform additional surgical tasks of different modalities.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; (b) a first suturing cartridge, wherein the cartridge receiving assembly is operable to removably receive the first suturing cartridge, wherein the first suturing cartridge comprises: (i) a first curved needle, wherein the first curved needle extends along an arc defined by a first radius of curvature, (ii) a first drive assembly, wherein the first drive assembly is operable to drive the first curved needle along an orbital path through a plurality of revolutions, and (iii) a first input feature, wherein the first input feature is configured to couple with the movable output of the cartridge receiving assembly, wherein the first input feature is configured to actuate the first drive assembly in response to movement of the movable output; and (c) a second suturing cartridge, wherein the cartridge receiving assembly is operable to removably receive the second suturing cartridge, wherein the second suturing cartridge comprises: (i) a second curved needle, wherein the second curved needle extends along an arc defined by a second radius of curvature, wherein the second radius of curvature is larger than the first radius of curvature, (ii) a second drive assembly, wherein the second drive assembly is operable to drive the second curved needle along an orbital path through a plurality of revolutions, and (iii) a second input feature, wherein the second input feature is configured to couple with the movable output of the cartridge receiving assembly, wherein the second input feature is configured to actuate the second drive assembly in response to movement of the movable output.

Example 2

The surgical kit of Example 1, further comprising a clip applier cartridge, wherein the cartridge receiving assembly is operable to removably receive the clip applier cartridge, wherein the clip applier cartridge comprises: (i) a clip, wherein the clip is configured to transition from an open configuration to a closed configuration, wherein the clip is configured to remain in the closed configuration upon transitioning from the open configuration to the closed configuration, (ii) a third drive assembly, wherein the third drive assembly is operable to drive the clip from the open configuration to the closed configuration, and (iii) a third input feature, wherein the third input feature is configured to couple with the movable output of the cartridge receiving assembly, wherein the third input feature is configured to actuate the third drive assembly in response to movement of the movable output.

Example 3

The surgical kit of Example 2, wherein the clip comprises a pair of legs and a crown joining the pair of legs together, wherein the third drive assembly comprises a pair of jaws operable to drive the legs toward each other to reach the closed configuration.

Example 4

The surgical kit of Example 3, wherein the clip comprises a malleable material, wherein the malleable material forming the clip is configured to hold the clip in the closed configuration upon transitioning from the open configuration to the closed configuration.

Example 5

The surgical kit of any one or more of Examples 2 through 4, wherein the clip comprises a pair of legs and a living hinge joining the pair of legs together, wherein the legs of the clip comprise complementary latching features that are configured to hold the clip in the closed configuration upon transitioning from the open configuration to the closed configuration.

Example 6

The surgical kit of any one or more of Examples 2 through 5, wherein the third drive assembly comprises a pair of jaws and a collar, wherein the collar is configured to transition between a proximal position and a distal position, wherein the jaws are configured to close in response to longitudinal movement of the collar to thereby transition the clip from the open configuration to the closed configuration.

Example 7

The surgical kit of Example 6, wherein the jaws are configured to close in response to proximal movement of the collar to thereby transition the clip from the open configuration to the closed configuration.

Example 8

The surgical kit of any one or more of Example 6, wherein the jaws are configured to close in response to distal movement of the collar to thereby transition the clip from the open configuration to the closed configuration.

Example 9

The surgical kit of any one or more of Examples 6 through 8, wherein the third drive assembly further comprises a rack and pinion assembly operable to drive the collar longitudinally.

Example 10

The surgical kit of Example 9, wherein the third input feature comprises a rotary input operable to rotate the pinion.

Example 11

The surgical kit of any one or more of Examples 2 through 10, wherein the clip applier cartridge further comprises a plurality of clips, wherein the third drive assembly is operable to drive a succession of the clips from the open configuration to the closed configuration.

Example 12

The surgical kit of Example 11, wherein the clip applier cartridge further comprises a retainer, wherein the retainer is operable to selectively retain one or more of the clips as the third drive assembly drives the succession of clips from the open configuration to the closed configuration.

Example 13

The surgical kit of Example 12, wherein the third drive assembly further comprises a pair of jaws, wherein the jaws are configured to close in response movement of the third input feature to thereby transition the clip from the open configuration to the closed configuration.

Example 14

The surgical kit of Example 13, wherein the retainer is configured to reciprocate longitudinally in response to movement of the third input feature to thereby successively index the clips in the succession relative to the jaws.

Example 15

The surgical kit of Example 14, wherein the clip applier cartridge further comprises a rack and pinion assembly, wherein the rack and pinion assembly is configured to reciprocate the retainer longitudinally in response to rotary movement of the third input feature.

Example 16

The surgical kit of any one or more of Examples 1 through 15, further comprising a grasper cartridge, wherein the cartridge receiving assembly is operable to removably receive the grasper cartridge, wherein the grasper cartridge comprises: (i) a pair of grasping jaws, wherein the grasping jaws are configured to transition from an open configuration to a closed configuration, (ii) a third drive assembly, wherein the third drive assembly is operable to drive the grasping jaws from the open configuration to the closed configuration, and (iii) a third input feature, wherein the third input feature is configured to couple with the movable output of the cartridge receiving assembly, wherein the third input feature is configured to actuate the third drive assembly in response to movement of the movable output.

Example 17

The surgical kit of Example 16, wherein the third drive assembly comprises a pair of links pivotably coupled with the pair of grasping jaws, wherein the links are operable to drive the grasping jaws from the open configuration to the closed configuration.

Example 18

The surgical kit of Example 17, wherein each of the links has a distal end and a proximal end, wherein the third drive assembly further comprises an actuator, wherein the distal end of each of the links is pivotably secured to a proximal end of a corresponding grasping jaw of the pair of grasping jaws, wherein the proximal end of each of the links is pivotably coupled with the actuator.

Example 19

The surgical kit of Example 18, wherein the actuator is configured to translate longitudinally in response to rotation of the third input feature to thereby drive the links.

Example 20

The surgical kit of Example 19, wherein the third drive assembly further comprises a rack and pinion assembly, wherein the rack is secured to the actuator, wherein the pinion is coupled with the third input feature such that the rack is configured to drive the actuator longitudinally in response to rotation of the third input feature.

Example 21

The surgical kit of any one or more of Examples 1 through 20, further comprising a scissor cartridge, wherein the cartridge receiving assembly is operable to removably receive the scissor cartridge, wherein the scissor cartridge comprises: (i) a pair of scissor blades, wherein the scissor blades are configured to transition from an open configuration to a closed configuration, (ii) third drive assembly, wherein the third drive assembly is operable to drive the scissor blades from the open configuration to the closed configuration, and (iii) a third input feature, wherein the third input feature is configured to couple with the movable output of the cartridge receiving assembly, wherein the third input feature is configured to actuate the third drive assembly in response to movement of the movable output.

Example 22

The surgical kit of Example 21, wherein the scissor blades are configured to cut tissue through a shearing action in response to movement of the scissor blades from the open configuration to the closed configuration.

Example 23

The surgical kit of any one or more of Examples 1 through 22, further comprising a stapling cartridge, wherein the cartridge receiving assembly is operable to removably receive the stapling cartridge, wherein the stapling cartridge comprises: (i) a plurality of staples, (ii) a staple driver, wherein the staple driver is operable to drive the staples distally, (iii) a third drive assembly, wherein the third drive assembly is operable to drive the staple driver distally, and (iv) a third input feature, wherein the third input feature is configured to couple with the movable output of the cartridge receiving assembly, wherein the third input feature is configured to actuate the third drive assembly in response to movement of the movable output.

Example 24

The surgical kit of Example 23, wherein each staple comprises a pair of legs and a crown, wherein the legs of each staple include preformed bends.

Example 25

The surgical kit of any one or more of Examples 23 through 24, wherein the stapling cartridge further comprises an anvil member, wherein the staple driver is configured to cooperate with the anvil member to deform the staples in response to distal movement of the staple driver.

Example 26

The surgical kit of Example 25, wherein each staple comprises a pair of legs and a crown, wherein the anvil member is configured to engage the crown.

Example 27

The surgical kit of Example 26, wherein the staple driver comprise a pair of distally projecting prongs, wherein the prongs are configured to bend the legs of a distal-most staple of the plurality of staples around the anvil member while the crown of the distal-most staple is engaged with the anvil member.

Example 28

The surgical kit of any one or more of Examples 25 through 47, wherein the stapling cartridge further comprises a guide member, wherein the guide member has an obliquely angled guide feature configured to guide a distal-most staple of the plurality of staples into engagement with the anvil member.

Example 29

The surgical kit of any one or more of Examples 25 through 47, wherein the stapling cartridge further comprises a biasing member configured to resiliently urge the staples distally.

Example 30

The surgical kit of Example 29, wherein the stapling cartridge further comprises a stop member configured to regulate distal positioning of staples by the biasing member.

Example 31

The surgical kit of Example 30, wherein the stop member comprises a leaf spring and a stop block, wherein the stop block is configured to arrest distal movement of the staples, wherein the leaf spring is configured to deform to allow a single staple to move distal to the stop block in each actuation of the stapling cartridge.

Example 32

The surgical kit of any one or more of Examples 1 through 31, wherein the body comprises a handle assembly.

Example 33

The surgical kit of Example 32, wherein the actuation input feature comprises a pivotable trigger.

Example 34

The surgical kit of any one or more of Examples 1 through 33, wherein the movable output feature is configured to rotate in response to activation of the actuation input feature.

Example 35

The surgical kit of Example 34, wherein the shaft assembly defines a longitudinal axis, wherein the movable output feature is configured to rotate about a rotation axis that is perpendicular to the longitudinal axis of the shaft assembly.

Example 36

The surgical kit of Example 35, wherein the first drive assembly comprises a first link operable to convert rotation of the first input feature into orbital motion of the first curved needle.

Example 37

The surgical kit of Example 36, wherein the first link is operable to convert rotation of the first input feature into orbital motion of the first curved needle about an orbit axis, wherein the orbit axis is perpendicular to the longitudinal axis of the shaft assembly.

Example 38

The surgical kit of Example 37, wherein the rotation axis is parallel to the orbit axis.

Example 39

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; and (b) a clip applier cartridge, wherein the cartridge receiving assembly is operable to removably receive the clip applier cartridge, wherein the clip applier cartridge comprises: (i) a clip, wherein the clip is configured to transition from an open configuration to a closed configuration, wherein the clip is configured to remain in the closed configuration upon transitioning from the open configuration to the closed configuration, (ii) a drive assembly, wherein the drive assembly is operable to drive the clip from the open configuration to the closed configuration, and (iii) an input feature, wherein the input feature is configured to couple with the movable output of the cartridge receiving assembly, wherein the input feature is configured to actuate the drive assembly in response to movement of the movable output.

Example 40

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; and (b) a grasper cartridge, wherein the cartridge receiving assembly is operable to removably receive the grasper cartridge, wherein the grasper cartridge comprises: (i) a pair of grasping jaws, wherein the grasping jaws are configured to transition from an open configuration to a closed configuration, (ii) a drive assembly, wherein the drive assembly is operable to drive the grasping jaws from the open configuration to the closed configuration, and (iii) an input feature, wherein the input feature is configured to couple with the movable output of the cartridge receiving assembly, wherein the input feature is configured to actuate the drive assembly in response to movement of the movable output.

Example 41

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; and (b) a scissor cartridge, wherein the cartridge receiving assembly is operable to removably receive the scissor cartridge, wherein the scissor cartridge comprises: (i) a pair of scissor blades, wherein the scissor blades are configured to transition from an open configuration to a closed configuration, (ii) a drive assembly, wherein the drive assembly is operable to drive the scissor blades from the open configuration to the closed configuration, and (iii) an input feature, wherein the input feature is configured to couple with the movable output of the cartridge receiving assembly, wherein the input feature is configured to actuate the drive assembly in response to movement of the movable output.

Example 42

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; and (b) a stapling cartridge, wherein the cartridge receiving assembly is operable to removably receive the stapling cartridge, wherein the stapling cartridge comprises: (i) a plurality of staples, (ii) a staple driver, wherein the staple driver is operable to drive the staples distally, (iii) a third drive assembly, wherein the third drive assembly is operable to drive the staple driver distally, and (iv) a third input feature, wherein the third input feature is configured to couple with the movable output of the cartridge receiving assembly, wherein the third input feature is configured to actuate the third drive assembly in response to movement of the movable output.

Example 43

A surgical kit comprising: (a) a surgical instrument, wherein the surgical instrument comprises: (i) a body, wherein the body comprises an actuation input feature, (ii) a shaft assembly extending distally from the body, and (iii) a cartridge receiving assembly located at a distal end of the shaft assembly, wherein the cartridge receiving assembly comprises a movable output feature, wherein the movable output feature is configured to move in response to activation of the actuation input feature; (b) at least two cartridges selected from the following cartridges: (i) a first suturing cartridge, wherein the cartridge receiving assembly is operable to removably receive the first suturing cartridge, wherein the first suturing cartridge comprises: (A) a first curved needle, wherein the first curved needle extends along an arc defined by a first radius of curvature, (B) a first drive assembly, wherein the first drive assembly is operable to drive the first curved needle along an orbital path through a plurality of revolutions, and (C) a first input feature, wherein the first input feature is configured to couple with the movable output of the cartridge receiving assembly, wherein the first input feature is configured to actuate the first drive assembly in response to movement of the movable output, and (ii) a second suturing cartridge, wherein the cartridge receiving assembly is operable to removably receive the second suturing cartridge, wherein the second suturing cartridge comprises: (A) a second curved needle, wherein the second curved needle extends along an arc defined by a second radius of curvature, wherein the second radius of curvature is larger than the first radius of curvature, (B) a second drive assembly, wherein the second drive assembly is operable to drive the second curved needle along an orbital path through a plurality of revolutions, and (C) a second input feature, wherein the second input feature is configured to couple with the movable output of the cartridge receiving assembly, wherein the second input feature is configured to actuate the second drive assembly in response to movement of the movable output, (iii) a clip applier cartridge, wherein the cartridge receiving assembly is operable to removably receive the clip applier cartridge, wherein the clip applier cartridge comprises: (A) a clip, wherein the clip is configured to transition from an open configuration to a closed configuration, wherein the clip is configured to remain in the closed configuration upon transitioning from the open configuration to the closed configuration, (B) a third drive assembly, wherein the third drive assembly is operable to drive the clip from the open configuration to the closed configuration, and (C) a third input feature, wherein the third input feature is configured to couple with the movable output of the cartridge receiving assembly, wherein the third input feature is configured to actuate the third drive assembly in response to movement of the movable output, (iv) a grasper cartridge, wherein the cartridge receiving assembly is operable to removably receive the grasper cartridge, wherein the grasper cartridge comprises: (A) a pair of grasping jaws, wherein the grasping jaws are configured to transition from an open configuration to a closed configuration, (B) a fourth drive assembly, wherein the third drive assembly is operable to drive the grasping jaws from the open configuration to the closed configuration, and (C) a fourth input feature, wherein the fourth input feature is configured to couple with the movable output of the cartridge receiving assembly, wherein the fourth input feature is configured to actuate the fourth drive assembly in response to movement of the movable output, (v) a scissor cartridge, wherein the cartridge receiving assembly is operable to removably receive the scissor cartridge, wherein the scissor cartridge comprises: (A) a pair of scissor blades, wherein the scissor blades are configured to transition from an open configuration to a closed configuration, (B) a fifth drive assembly, wherein the third drive assembly is operable to drive the scissor blades from the open configuration to the closed configuration, and (C) a fifth input feature, wherein the fifth input feature is configured to couple with the movable output of the cartridge receiving assembly, wherein the fifth input feature is configured to actuate the fifth drive assembly in response to movement of the movable output, and (vi) a stapling cartridge, wherein the cartridge receiving assembly is operable to removably receive the stapling cartridge, wherein the stapling cartridge comprises: (A) a plurality of staples, (B) a staple driver, wherein the staple driver is operable to drive the staples distally, (C) third drive assembly, wherein the third drive assembly is operable to drive the staple driver distally, and (D) a third input feature, wherein the third input feature is configured to couple with the movable output of the cartridge receiving assembly, wherein the third input feature is configured to actuate the third drive assembly in response to movement of the movable output.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical kit comprising:
   (a) a surgical instrument, wherein the surgical instrument comprises:
      (i) a body, wherein the body comprises an actuation input feature,
      (ii) a shaft assembly extending distally from the body, and
      (iii) a cartridge receiving assembly located at a distal end of the shaft assembly, wherein the cartridge receiving assembly comprises a movable output feature, wherein the movable output feature is configured to move in response to activation of the actuation input feature;
(b) a first suturing cartridge, wherein the cartridge receiving assembly is operable to removably receive the first suturing cartridge, wherein the first suturing cartridge comprises:
(i) a first curved needle, wherein the first curved needle extends along an arc defined by a first radius of curvature,
(ii) a first drive assembly, wherein the first drive assembly is operable to drive the first curved needle along an orbital path through a plurality of revolutions, and
(iii) a first input feature, wherein the first input feature is configured to couple with the movable output of the cartridge receiving assembly, wherein the first input feature is configured to actuate the first drive assembly in response to movement of the movable output; and
(c) a second suturing cartridge, wherein the cartridge receiving assembly is operable to removably receive the second suturing cartridge, wherein the second suturing cartridge comprises:
(i) a second curved needle, wherein the second curved needle extends along an arc defined by a second radius of curvature, wherein the second radius of curvature is larger than the first radius of curvature,
(ii) a second drive assembly, wherein the second drive assembly is operable to drive the second curved needle along an orbital path through a plurality of revolutions, and
(iii) a second input feature, wherein the second input feature is configured to couple with the movable output of the cartridge receiving assembly, wherein the second input feature is configured to actuate the second drive assembly in response to movement of the movable output.

2. The surgical kit of claim 1, further comprising a clip applier cartridge, wherein the cartridge receiving assembly is operable to removably receive the clip applier cartridge, wherein the clip applier cartridge comprises:
(i) a clip, wherein the clip is configured to transition from an open configuration to a closed configuration, wherein the clip is configured to remain in the closed configuration upon transitioning from the open configuration to the closed configuration,
(ii) a third drive assembly, wherein the third drive assembly is operable to drive the clip from the open configuration to the closed configuration, and
(iii) a third input feature, wherein the third input feature is configured to couple with the movable output of the cartridge receiving assembly, wherein the third input feature is configured to actuate the third drive assembly in response to movement of the movable output.

3. The surgical kit of claim 2, wherein the third drive assembly comprises a pair of jaws and a collar, wherein the collar is configured to transition between a proximal position and a distal position, wherein the jaws are configured to close in response to longitudinal movement of the collar to thereby transition the clip from the open configuration to the closed configuration.

4. The surgical kit of claim 3, wherein the third drive assembly further comprises a rack and pinion assembly operable to drive the collar longitudinally.

5. The surgical kit of claim 2, wherein the clip applier cartridge further comprises a plurality of clips, wherein the third drive assembly is operable to drive a succession of the clips from the open configuration to the closed configuration.

6. The surgical kit of claim 5, wherein the clip applier cartridge further comprises a retainer, wherein the retainer is operable to selectively retain one or more of the clips as the third drive assembly drives the succession of clips from the open configuration to the closed configuration.

7. The surgical kit of claim 6, wherein the third drive assembly further comprises a pair of jaws, wherein the jaws are configured to close in response movement of the third input feature to thereby transition the clip from the open configuration to the closed configuration.

8. The surgical kit of claim 7, wherein the retainer is configured to reciprocate longitudinally in response to movement of the third input feature to thereby successively index the clips in the succession relative to the jaws.

9. The surgical kit of claim 8, wherein the clip applier cartridge further comprises a rack and pinion assembly, wherein the rack and pinion assembly is configured to reciprocate the retainer longitudinally in response to rotary movement of the third input feature.

10. The surgical kit of claim 1, further comprising a grasper cartridge, wherein the cartridge receiving assembly is operable to removably receive the grasper cartridge, wherein the grasper cartridge comprises:
(i) a pair of grasping jaws, wherein the grasping jaws are configured to transition from an open configuration to a closed configuration,
(ii) a third drive assembly, wherein the third drive assembly is operable to drive the grasping jaws from the open configuration to the closed configuration, and
(iii) a third input feature, wherein the third input feature is configured to couple with the movable output of the cartridge receiving assembly, wherein the third input feature is configured to actuate the third drive assembly in response to movement of the movable output.

11. The surgical kit of claim 10, wherein the third drive assembly comprises a pair of links pivotably coupled with the pair of grasping jaws, wherein the links are operable to drive the grasping jaws from the open configuration to the closed configuration, wherein each of the links has a distal end and a proximal end, wherein the third drive assembly further comprises an actuator, wherein the distal end of each of the links is pivotably secured to a proximal end of a corresponding grasping jaw of the pair of grasping jaws, wherein the proximal end of each of the links is pivotably coupled with the actuator, wherein the actuator is configured to translate longitudinally in response to rotation of the third input feature to thereby drive the links.

12. The surgical kit of claim 1, further comprising a scissor cartridge, wherein the cartridge receiving assembly is operable to removably receive the scissor cartridge, wherein the scissor cartridge comprises:
(i) a pair of scissor blades, wherein the scissor blades are configured to transition from an open configuration to a closed configuration,
(ii) a third drive assembly, wherein the third drive assembly is operable to drive the scissor blades from the open configuration to the closed configuration, and
(iii) a third input feature, wherein the third input feature is configured to couple with the movable output of the cartridge receiving assembly, wherein the third input feature is configured to actuate the third drive assembly in response to movement of the movable output.

13. The surgical kit of claim 1, further comprising a stapling cartridge, wherein the cartridge receiving assembly is operable to removably receive the stapling cartridge, wherein the stapling cartridge comprises:
(i) a plurality of staples,
(ii) a staple driver, wherein the staple driver is operable to drive the staples distally,
(iii) a third drive assembly, wherein the third drive assembly is operable to drive the staple driver distally, and
(iv) a third input feature, wherein the third input feature is configured to couple with the movable output of the cartridge receiving assembly, wherein the third input feature is configured to actuate the third drive assembly in response to movement of the movable output.

14. The surgical kit of claim 13, wherein the stapling cartridge further comprises:
(i) an anvil member, wherein the staple driver is configured to cooperate with the anvil member to deform the staples in response to distal movement of the staple driver, and
(ii) a guide member, wherein the guide member has an obliquely angled guide feature configured to guide a distal-most staple of the plurality of staples into engagement with the anvil member.

15. The surgical kit of claim 1, wherein the movable output feature is configured to rotate in response to activation of the actuation input feature.

16. The surgical kit of claim 15, wherein the shaft assembly defines a longitudinal axis, wherein the movable output feature is configured to rotate about a rotation axis that is perpendicular to the longitudinal axis of the shaft assembly.

17. The surgical kit of claim 16, wherein the first drive assembly comprises a first link operable to convert rotation of the first input feature into orbital motion of the first curved needle.

18. The surgical kit of claim 17, wherein the first link is operable to convert rotation of the first input feature into orbital motion of the first curved needle about an orbit axis, wherein the orbit axis is perpendicular to the longitudinal axis of the shaft assembly.

19. A surgical kit comprising:
(a) a surgical instrument, wherein the surgical instrument comprises:
(i) a body, wherein the body comprises an actuation input feature,
(ii) a shaft assembly extending distally from the body, and
(iii) a cartridge receiving assembly located at a distal end of the shaft assembly, wherein the cartridge receiving assembly comprises a movable output feature, wherein the movable output feature is configured to move in response to activation of the actuation input feature; and
(b) a clip applier cartridge, wherein the cartridge receiving assembly is operable to removably receive the clip applier cartridge, wherein the clip applier cartridge comprises:
(i) a clip, wherein the clip is configured to transition from an open configuration to a closed configuration, wherein the clip is configured to remain in the closed configuration upon transitioning from the open configuration to the closed configuration,
(ii) a drive assembly, wherein the drive assembly is operable to drive the clip from the open configuration to the closed configuration, and
(iii) an input feature, wherein the input feature is configured to couple with the movable output of the cartridge receiving assembly, wherein the input feature is configured to actuate the drive assembly in response to movement of the movable output.

20. A surgical kit comprising:
(a) a surgical instrument, wherein the surgical instrument comprises:
(i) a body, wherein the body comprises an actuation input feature,
(ii) a shaft assembly extending distally from the body, and
(iii) a cartridge receiving assembly located at a distal end of the shaft assembly, wherein the cartridge receiving assembly comprises a movable output feature, wherein the movable output feature is configured to move in response to activation of the actuation input feature;
(b) at least two cartridges selected from the following cartridges:
(i) a first suturing cartridge, wherein the cartridge receiving assembly is operable to removably receive the first suturing cartridge, wherein the first suturing cartridge comprises:
(A) a first curved needle, wherein the first curved needle extends along an arc defined by a first radius of curvature,
(B) a first drive assembly, wherein the first drive assembly is operable to drive the first curved needle along an orbital path through a plurality of revolutions, and
(C) a first input feature, wherein the first input feature is configured to couple with the movable output of the cartridge receiving assembly, wherein the first input feature is configured to actuate the first drive assembly in response to movement of the movable output, and
(ii) a second suturing cartridge, wherein the cartridge receiving assembly is operable to removably receive the second suturing cartridge, wherein the second suturing cartridge comprises:
(A) a second curved needle, wherein the second curved needle extends along an arc defined by a second radius of curvature, wherein the second radius of curvature is larger than the first radius of curvature,
(B) a second drive assembly, wherein the second drive assembly is operable to drive the second curved needle along an orbital path through a plurality of revolutions, and
(C) a second input feature, wherein the second input feature is configured to couple with the movable output of the cartridge receiving assembly, wherein the second input feature is configured to actuate the second drive assembly in response to movement of the movable output,
(iii) a clip applier cartridge, wherein the cartridge receiving assembly is operable to removably receive the clip applier cartridge, wherein the clip applier cartridge comprises:
(A) a clip, wherein the clip is configured to transition from an open configuration to a closed configuration, wherein the clip is configured to remain in the closed configuration upon transitioning from the open configuration to the closed configuration,
(B) a third drive assembly, wherein the third drive assembly is operable to drive the clip from the open configuration to the closed configuration, and (C) a third input feature, wherein the third input feature is configured to couple with the movable output of the cartridge receiving assembly, wherein the third input feature is configured to actuate the third drive assembly in response to movement of the movable output, (iv) a grasper cartridge, wherein the cartridge receiving assembly is operable to removably receive the grasper cartridge, wherein the grasper cartridge comprises:
  (A) a pair of grasping jaws, wherein the grasping jaws are configured to transition from an open configuration to a closed configuration,
  (B) a fourth drive assembly, wherein the third drive assembly is operable to drive the grasping jaws from the open configuration to the closed configuration, and
  (C) a fourth input feature, wherein the fourth input feature is configured to couple with the movable output of the cartridge receiving assembly, wherein the fourth input feature is configured to actuate the fourth drive assembly in response to movement of the movable output, (v) a scissor cartridge, wherein the cartridge receiving assembly is operable to removably receive the scissor cartridge, wherein the scissor cartridge comprises:
  (A) a pair of scissor blades, wherein the scissor blades are configured to transition from an open configuration to a closed configuration,
  (B) a fifth drive assembly, wherein the third drive assembly is operable to drive the scissor blades from the open configuration to the closed configuration, and
  (C) a fifth input feature, wherein the fifth input feature is configured to couple with the movable output of the cartridge receiving assembly, wherein the fifth input feature is configured to actuate the fifth drive assembly in response to movement of the movable output, and (vi) a stapling cartridge, wherein the cartridge receiving assembly is operable to removably receive the stapling cartridge, wherein the stapling cartridge comprises:
  (A) a plurality of staples,
  (B) a staple driver, wherein the staple driver is operable to drive the staples distally,
  (C) a third drive assembly, wherein the third drive assembly is operable to drive the staple driver distally, and
  (D) a third input feature, wherein the third input feature is configured to couple with the movable output of the cartridge receiving assembly, wherein the third input feature is configured to actuate the third drive assembly in response to movement of the movable output.

* * * * *